US012268757B2

(12) United States Patent
Polasek et al.

(10) Patent No.: US 12,268,757 B2
(45) Date of Patent: Apr. 8, 2025

(54) CYCLEN BASED COMPOUNDS, COORDINATION COMPOUNDS, PEPTIDES, PHARMACEUTICAL PREPARATION, AND USE THEREOF

(71) Applicant: USTAV ORGANICKE CHEMIE A BIOCHEMIE AV CR V.V.I., Prague (CZ)

(72) Inventors: Miloslav Polasek, Prague (CZ); Jan Kretschmer, Prague (CZ)

(73) Assignee: USTAV ORGANICKE CHEMIE A BIOCHEMIE AV CR V.V.I., Prague (CZ)

( * ) Notice: Subject to any disclaimer, the term of this patent is extended or adjusted under 35 U.S.C. 154(b) by 791 days.

(21) Appl. No.: 17/609,979

(22) PCT Filed: May 27, 2020

(86) PCT No.: PCT/CZ2020/050032
§ 371 (c)(1),
(2) Date: Nov. 9, 2021

(87) PCT Pub. No.: WO2020/259726
PCT Pub. Date: Dec. 30, 2020

(65) Prior Publication Data
US 2022/0218849 A1   Jul. 14, 2022

(30) Foreign Application Priority Data
Jun. 25, 2019 (EP) .................................... 19182286

(51) Int. Cl.
| A61K 49/10 | (2006.01) |
| A61K 49/14 | (2006.01) |
| C07D 403/04 | (2006.01) |
| C07D 403/14 | (2006.01) |
| C07F 5/00 | (2006.01) |
| C07K 5/078 | (2006.01) |

(52) U.S. Cl.
CPC ............. *A61K 49/106* (2013.01); *A61K 49/14* (2013.01); *C07D 403/04* (2013.01); *C07D 403/14* (2013.01); *C07F 5/003* (2013.01); *C07K 5/06139* (2013.01)

(58) Field of Classification Search
None
See application file for complete search history.

(56) References Cited

FOREIGN PATENT DOCUMENTS

| WO | 0177102 A1 | 10/2001 |
| WO | 03013617 A2 | 2/2003 |

OTHER PUBLICATIONS

Rohrer Martin et al: "Comparison of magnetic properties of MRI contrast media solutions at different magnetic field strengths", Investigative Radiology, Lippincott Williams & Wilkins, US, vol. 40, No. 11, Nov. 1, 2005 (Nov. 1, 2005), pp. 715-724, XP009154777,ISSN: 0020-9996, abstract retrieved Nov. 4, 2021.
International Search Report and Written Opinion for corresponding PCT application No. PCT/CZ2020/050032, mailed Jul. 10, 2020.

*Primary Examiner* — Michael G. Hartley
*Assistant Examiner* — Samantha L Mejias
(74) *Attorney, Agent, or Firm* — NOTARO, MICHALOS & ZACCARIA P.C.

(57) ABSTRACT

Cyclen based compounds of general formula (I) are disclosed. X is nitrogen and Y, Z are —CH—, or X, Z are —CH— and Y is nitrogen, or X, Y are —CH— and Z is nitrogen. $R^1$ is independently selected from H; COOH; benzyloxycarbonyl; fluorenylmethyloxycarbonyl; tert-butoxycarbonyl; methylcarbonyl; trifluoromethylcarbonyl; benzyl; triphenylmethyl; tosyl; mesyl; benzyloxymethyl; phenylsulfonyl; ethoxycarbonyl; 2,2,2-trichloroethyloxycarbonyl; methoxycarbonyl; methoxymethyloxycarbonyl; $R^2$ is selected from H; methylcarbonyl; tert-butyldimethylsilyl; (C1-C4)alkyl; $R_3$ is independently selected from H; (C1-C6)alkyl.

11 Claims, No Drawings
Specification includes a Sequence Listing.

CYCLEN BASED COMPOUNDS, COORDINATION COMPOUNDS, PEPTIDES, PHARMACEUTICAL PREPARATION, AND USE THEREOF

TECHNICAL FIELD

This invention relates to cyclen based compounds suitable for stable incorporation of rare earth elements into peptides. The present invention further relates to peptides comprising cyclen based compounds or their complexes with rare earth elements, and to pharmaceutical preparations suitable for MRI or MRI/PET as contrast agents.

BACKGROUND ART

Metal elements find many biomedical applications, mainly as part of imaging contrast agents or radiotherapeutic agents for treatment of cancer. The metal serves as a source of a signal (for imaging purposes) or provides a therapeutic effect through its radioactive decay. For many of these applications, it is necessary to bind the metal in a stable chelate to suppress the toxicity of the free metal ions and/or in order to link the metal to a targeting vector (most commonly a peptide or antibody) for directed delivery to specific molecular targets in vivo. This connection can be achieved with bifunctional chelators that fulfill two functions: (i) bind the metal ion, and (ii) allow covalent attachment to peptides and other organic molecules.

Rare earth elements (scandium—Sc, yttrium—Y, lanthanum—La, cerium—Ce, praseodymium—Pr, neodymium—Nd, promethium—Pm, samarium—Sm, europium—Eu, gadolinium—Gd, terbium—Tb, dysprosium—Dy, holmium—Ho, erbium—Er, thulium—Tm, ytterbium—Yb and lutetium—Lu) are a group of metals that offer a broad range of medical applications. Radionuclides of these elements find use in radiopharmaceuticals. Radiopharmaceuticals based on $^{90}$Y, $^{153}$Sm and $^{177}$Lu are approved by FDA, clinical trials are ongoing with $^{166}$Ho, and others show advantageous properties for Positron Emission Tomography (PET), Single-Photon Emission Computed Tomography (SPECT) or therapy ($^{44}$Sc, $^{47}$Sc, $^{86}$Y, $^{149}$Pm, $^{159}$Gd, $^{149}$Tb, $^{161}$T, $^{165}$Dy, $^{161}$Ho, $^{169}$Er and $^{175}$Yb). Stable, non-radioactive Gd chelates are in clinical use as contrast agents for Magnetic Resonance Imaging (MRI) already for several decades. The rare earth elements are chemically similar, providing the advantage that the same targeting vector, bioconjugation strategy and labelling chemistry can be used with any member of the group.

A number of approaches have been developed to conjugate stable chelates of rare earth elements to peptide chains (De León-Rodriguez L. M., Kovacs Z. (2008), *Bioconjugate Chem.* 19(2), 391-402). The most common approach is to first synthesize a complete peptide chain by solid-phase peptide synthesis (i.e. on resin support), de-protect and cleave the peptide from the solid support, purify the product and then perform the conjugation step, followed by yet another purification of the conjugate. Usually, a bifunctional chelator is used for the conjugation, followed by complexation of the metal at the last step. If permitted by the conjugation chemistry, the complexation can be done first, followed by conjugation of the metal chelate to the peptide. However, this is not possible when the functional group needed for conjugation (e.g. carboxylic group for peptide coupling) becomes coordinated to the metal ion, which makes it unreactive for the conjugation reaction. A disadvantage of this approach arises whenever the conjugation may occur at multiple positions on the peptide molecule, resulting in a mixture of products that need to be separated.

A much less common synthetic approach is to employ chelators that bear both amino group and carboxylic group and use them as unnatural amino acid building blocks during the peptide synthesis. Thus, the chelator becomes embedded within the peptide chain. The advantage is that the position of the chelator within the peptide sequence is well defined, given by the sequence of synthetic steps. Furthermore, no conjugation step is needed after the peptide synthesis. Complexation of metal ion is still needed as the last step. An example of this approach is the amino acid chelator DOTAla that was used to synthesize high-relaxivity MRI contrast agents (Boros E. et al. (2012), *J. Am. Chem. So.* 134(48), 19858-19868). Several other examples were reported (De León-Rodriguez L. M. et al. (2004), *Chem. Eur. J.,* 10(5), 1149-1155; Yoo B., Pagel M. D. (2007), *Bioconjugate Chem.* 18, 903-911).

An alternative use of amino acid chelators is to form a metal chelate first that is then used as a building block during the peptide synthesis. Thus, a metal chelate becomes embedded within the peptide sequence. With this approach, there is no need for conjugation nor for complexation after the peptide synthesis, thus greatly simplifying the overall synthetic procedure. Furthermore, the position of the metal chelate is well defined. In principle, it is also possible to embed multiple chelates of different metals within the same peptide sequence and maintain precise control over position of each metal chelate. This is not possible to achieve with any of the abovementioned approaches. The necessary condition for this approach to work is that the carboxylic group needed for the peptide coupling must not coordinate to the metal ion, otherwise it would become unreactive for the coupling reaction. Thus, the carboxylic group must be distanced from the metal ion. Bruckner et al. solved this problem by attaching chelator DOTA to the side-chain of lysine (Brückner, K. et al. (2014). *Bioconjugate Chem.* 25, 1069-1077). In this way, they spatially separated the chelator part of the building block from the amino acid part. The resulting building blocks maintained reactivity towards peptide synthesis while carrying metal chelates.

The ability to combine different metals within one peptide-based molecule is important for synthesis of new advanced imaging or therapeutic agents. For example, Gd(III) may be combined with positron-emitting radionuclide (e.g. $^{44}$Sc, $^{86}$Y) to provide dual MRI/PET contrast agents. Combination of Gd(III) and therapeutic radionuclides (e.g. $^{177}$Lu, $^{161}$Tb, $^{90}$Y) can provide theranostic (therapeutic+diagnostic) agents. Maintaining control over the positions of the metals is crucial, since by randomizing their positions one would obtain a mixture of different products. Furthermore, restricting the conformational and rotational flexibility of the metal chelates is important for functionality of gadolinium-based MRI contrast agents. It is well known that the efficiency of these contrast agents (called relaxivity) depends on several physico-chemical parameters, one of which being rotational motion (Caravan P. et al. (2009), *Contrast Media Mol. Imaging* 4, 89-100). Restricting the rotational motion of Gd(III) chelates is the most effective way to increase the relaxivity. However, controlling this parameter is very difficult. Such control can be achieved by incorporating the Gd(III) chelates into peptide chains, provided that the connection between the peptide backbone and the chelate does not permit rotation. However, this condition is difficult to fulfill, since the connection must be extremely rigid. In addition, the metal chelates must be exceptionally stable and inert to not release the toxic metal ions in vivo. None of the examples of chelator building blocks mentioned above fulfills all these criteria. The combination of requirements, i.e. allowing multiple metals within one peptide molecule while maintaining control over their position and rotational motion, remains an unmet need.

DISCLOSURE OF INVENTION

The amino acid chelator building blocks disclosed in this invention combine multiple advantages, as they: (1) provide stable metal chelates with rare earth elements, (2) can be incorporated into peptide chains by means of standard solid-phase peptide synthesis, (3) can be incorporated into peptide chains either in the form of protected chelator, or in the form of a metal chelate, (4) allow combining different metals within a single peptide molecule while maintaining control over the positions of the metals, (5) if incorporated into peptide chains in the form of protected chelator, can be de-protected and used for additional (post peptide synthesis) complexation of metal ions, (6) do not permit free rotation of the metal chelates independent of the peptide chain, (7) are stereochemically well-defined molecules.

The compounds disclosed in this invention are synthesized from two main parts that provide significant advantages. The amino acid part of the molecule originates from synthetic precursors that have well defined structure of chiral centers. Control over chirality, regio- and stereo-isomerism is maintained throughout the synthesis, or the arising isomers can be separated by means of (non-chiral) chromatography. The second part of the compounds originates from the macrocyclic cyclen (1,4,7,10-tetraazacyclododecane) that is substituted with acetate donor arms. This is a well-known structural motif that ensures high stability of metal chelates. Both parts (macrocycle and amino acid) are connected directly (covalent bond), avoiding lengthy linkers that would allow rotation along this connection. Another important feature is that an —OR$^2$ group, such as hydroxyl group, is present on the amino acid part of the molecule, positioned in such a way as to allow its coordination to the metal ion in the chelator part. The amino acid part of the molecule thus provides two possible donor atoms, either the oxygen atom of the —OR$^2$ group (such as hydroxyl group), or an oxygen atom of the carboxylic group (where R$^1$ bound to X is COOH). This further restricts the conformational flexibility and rotational motion of the resulting metal chelates incorporated within peptide chains. A variety of protective groups can be utilized in these compounds to make them usable as building blocks for peptide synthesis.

The object of the present invention is a cyclen based compound of general formula (I),

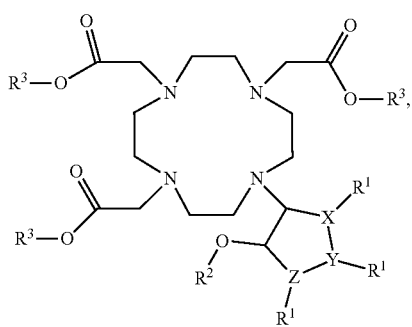

(I)

wherein

X is nitrogen and Y, Z are —CH—, or X, Z are —CH— and Y is nitrogen, or X, Y are —CH— and Z is nitrogen;

R$^1$ is independently selected from H; COOH; benzyloxycarbonyl; fluorenylmethyloxycarbonyl; tert-butoxycarbonyl; methylcarbonyl; trifluoromethylcarbonyl; benzyl; triphenylmethyl; tosyl; mesyl; benzyloxymethyl; phenylsulfonyl; ethoxycarbonyl; 2,2,2-trichloroethyloxycarbonyl; methoxycarbonyl; methoxymethyloxycarbonyl;

R$^2$ is selected from H; methylcarbonyl; tert-butyldimethylsilyl; (C1-C4)alkyl, which can be linear or branched, and which can optionally be substituted with CH$_3$O—, CH$_3$S—; oxacyclohexyl; allyl; tert-butyldiphenylsilyl; tert-butylcarbonyl; phenylcarbonyl; nitrobenzyl; benzyloxymethyl, which can optionally be substituted with CH$_3$O—, —NO$_2$; fluorenylmethyloxycarbonyl; trichlorocarbonyl; trifluorocarbonyl; benzyl; tosyl; mesyl; phenylsulfonyl; allylsulphonyl; ethoxycarbonyl; 2,2,2-trichloroethyloxycarbonyl; methoxycarbonyl; methoxymethyloxycarbonyl;

R$^3$ is independently selected from H; (C1-C6)alkyl, which can be linear or branched, and which can optionally be substituted with —CH$_3$, —Cl, —F, —CN, tosyl, triisopropylsilyl, CH$_3$O—, CH$_3$S—; (C5-C6)cycloalkyl, which can optionally be substituted with —CH$_3$, —Cl, —F, —CN; (C6-C10)aryl, which can optionally be substituted with —CH$_3$, —Cl, —F, —CN; allyl, propargyl; fluorenylmethyl; benzoylmethyl; phenyloxymethyl; oxacyclopentyl; 2-oxo-1,2-diphenylethyl;

with the proviso that where R$^1$ is bound to nitrogen, then R$^1$ is not COOH;

with the proviso that where R$^1$ is bound to —CH—, then R$^1$ is independently H or COOH;

and with the proviso that one R$^1$ is COOH, and one —CH—R$^1$ group is —CH$_2$—.

The cyclen based compounds of general formula (I) serve as precursors for metal chelates, and they are especially suitable for coordination to rare earth elements, such se lanthanides, or Y and Sc (scandium—Sc, yttrium—Y, lanthanum—La, cerium—Ce, praseodymium—Pr, neodymium—Nd, promethium—Pm, samarium—Sm, europium—Eu, gadolinium—Gd, terbium—Tb, dysprosium—Dy, holmium—Ho, erbium—Er, thulium—Tm, ytterbium—Yb and lutetium—Lu).

The general formula (I) of the present invention is meant to include all isomers, enantiomers and diastereoisomers.

In one preferred embodiment, Y is nitrogen, X—R$^1$ is —CH$_2$—, and Z—R$^1$ is —CH(COOH).

In one preferred embodiment, Y is nitrogen, X—R$^1$ is —CH(COOH)—, and Z—R$^1$ is —CH$_2$—.

In one preferred embodiment, X is nitrogen, Y—R$^1$ is —CH(COOH)—, and Z—R$^1$ is —CH$_2$—.

In one preferred embodiment, X—R$^1$ is —CH$_2$—, Y—R$^1$ is —CH(COOH)—, and Z is nitrogen.

In one embodiment, substituent R$^1$ is preferably selected from H, COOH, benzyloxycarbonyl and fluorenylmethyloxycarbonyl.

In one embodiment, substituent R$^2$ is selected from H, methylcarbonyl and tert-butyldimethylsilyl.

In one embodiment, substituent R$^3$ is selected from H, methyl and tert-butyl.

In one embodiment, the cyclen based compound of general formula (I) according to the present invention is selected from the group consisting of:

(2S,3S,4S)-4-hydroxy-3-(4,7,10-tris(2-(tert-butoxy)-2-oxoethyl)-1,4,7,10-tetraazacyclododecan-1-yl)pyrrolidine-2-carboxylic acid (1g);

(2S,3R,4R)-3-hydroxy-4-(4,7,10-tris(2-(tert-butoxy)-2-oxo-ethyl)-1,4,7,10-tetraazacyclododecan-1-yl)pyrrolidine-2-carboxylic acid (1h);

(2S,3S,4S)-1-(((9H-fluoren-9-yl)methoxy)carbonyl)-4-hydroxy-3-(4,7,10-tris(2-(tert-butoxy)-2-oxoethyl)-1,4,7,10-tetraazacyclododecan-1-yl)pyrrolidine-2-carboxylic acid (2);

2,2',2''-(10-((2S,3S,4S)-1-(2-(9H-fluoren-9-yl)acetoxy)-2-carboxy-4-hydroxypyrrolidin-3-yl)-1,4,7,10-tetraazacyclododecane-1,4,7-triyl)triacetic acid (3);

(2S,3S,4S)-4-acetoxy-3-(4,7,10-tris(2-(tert-butoxy)-2-oxoethyl)-1,4,7,10-tetraazacyclododecan-1-yl)pyrrolidine-2-carboxylic acid (7c);

(2S,3R,4R)-3-acetoxy-4-(4,7,10-tris(2-(tert-butoxy)-2-oxoethyl)-1,4,7,10-tetraazacyclododecan-1-yl)pyrrolidine-2-carboxylic acid (7d);

(2S,3S,4S)-1-(((9H-fluoren-9-yl)methoxy)carbonyl)-4-acetoxy-3-(4,7,10-tris(2-(tert-butoxy)-2-oxoethyl)-1,4,7,10-tetraazacyclododecan-1-yl)pyrrolidine-2-carboxylic acid (8);

2,2',2''-(10-((2S,3S,4S)-1-(((9H-fluoren-9-yl)methoxy)carbonyl)-4-acetoxy-2-carboxypyrrolidin-3-yl)-1,4,7,10-tetraazacyclododecane-1,4,7-triyl)triacetic acid (9);

(2S,3S,4S)-4-acetoxy-3-(4,7,10-tris(2-methoxy-2-oxoethyl)-1,4,7,10-tetraazacyclododecan-1-yl)pyrrolidine-2-carboxylic acid (11e);

(2S,3R,4R)-3-acetoxy-4-(4,7,10-tris(2-methoxy-2-oxoethyl)-1,4,7,10-tetraazacyclododecan-1-yl)pyrrolidine-2-carboxylic acid (11f);

(2S,3S,4S)-1-(((9H-fluoren-9-yl)methoxy)carbonyl)-4-acetoxy-3-(4,7,10-tris(2-methoxy-2-oxoethyl)-1,4,7,10-tetraazacyclododecan-1-yl)pyrrolidine-2-carboxylic acid (12);

(2S,3S,4S)-4-((tert-butyldimethylsilyl)oxy)-3-(4,7,10-tris(2-(tert-butoxy)-2-oxoethyl)-1,4,7,10-tetraazacyclododecan-1-yl)pyrrolidine-2-carboxylic acid (13c);

(2S,3R,4R)-3-((tert-butyldimethylsilyl)oxy)-4-(4,7,10-tris(2-(tert-butoxy)-2-oxoethyl)-1,4,7,10-tetraazacyclododecan-1-yl)pyrrolidine-2-carboxylic acid (13d);

(2S,3S,4S)-1-(((9H-fluoren-9-yl)methoxy)carbonyl)-4-((tert-butyldimethylsilyl)oxy)-3-(4,7,10-tris(2-(tert-butoxy)-2-oxoethyl)-1,4,7,10-tetraazacyclododecan-1-yl)pyrrolidine-2-carboxylic acid (14);

(2R,3S,4S)-4-hydroxy-3-(4,7,10-tris(2-(tert-butoxy)-2-oxoethyl)-1,4,7,10-tetraazacyclododecan-1-yl)pyrrolidine-2-carboxylic acid (15e):

(2R,3R,4R)-3-hydroxy-4-(4,7,10-tris(2-(tert-butoxy)-2-oxoethyl)-1,4,7,10-tetraazacyclododecan-1-yl)pyrrolidine-2-carboxylic acid (15f;

(2R,3S,4S)-1-(((9H-fluoren-9-yl)methoxy)carbonyl)-4-hydroxy-3-(4,7,10-tris(2-(tert-butoxy)-2-oxoethyl)-1,4,7,10-tetraazacyclododecan-1-yl)pyrrolidine-2-carboxylic acid (16);

(2R,3S,4R)-1-(((9H-fluoren-9-yl)methoxy)carbonyl)-3-hydroxy-4-(4,7,10-tris(2-(tert-butoxy)-2-oxoethyl)-1,4,7,10-tetraazacyclododecan-1-yl)pyrrolidine-2-carboxylic acid (17);

2,2',2''-(10-((2R,3S,4S)-1-(((9H-fluoren-9-yl)methoxy)carbonyl)-2-carboxy-4-hydroxypyrrolidin-3-yl)-1,4,7,10-tetraazacyclododecane-1,4,7-triyl)triacetic acid (18);

2,2',2''-(10-((3R,4S,5R)-1-(((9H-fluoren-9-yl)methoxy)carbonyl)-5-carboxy-4-hydroxypyrrolidin-3-yl)-1,4,7,10-tetraazacyclododecane-1,4,7-triyl)triacetic acid (19).

In general, compounds of general formula (I) according to the present invention represent chelators with protected carboxylic and amino groups. In order to form metal chelates, $R^3$ groups of the cyclen based compounds of general formula (I) should be de-protected. Examples of de-protecting reactions are acidic hydrolysis, for example using trifluoroacetic acid (suitable for tert-butyl protecting group), hydrogenation using Pd on active carbon (suitable for benzyl and benzyloxycarbonyl protecting groups), basic hydrolysis using aqueous lithium hydroxide (suitable for methyl ester protecting groups).

Another object of the present invention is a coordination compound of general formula (Ia),

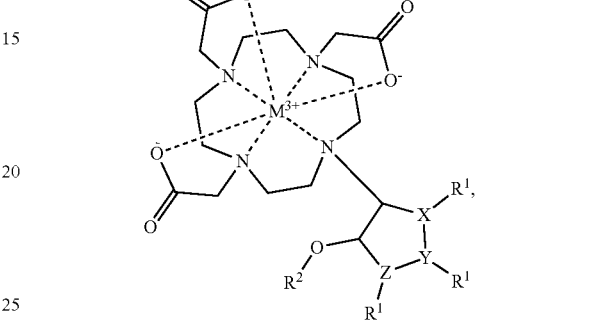

wherein

X is nitrogen and Y, Z are —CH—, or X, Z are —CH— and Y is nitrogen, or X, Y are —CH— and Z is nitrogen;

$R^1$ is independently selected from H; COOH; benzyloxycarbonyl; fluorenylmethyloxycarbonyl; tert-butoxycarbonyl; methylcarbonyl; trifluoromethylcarbonyl; benzyl; triphenylmethyl; tosyl; mesyl; benzyloxymethyl; phenylsulfonyl; ethoxycarbonyl; 2,2,2-trichloroethyloxycarbonyl; methoxycarbonyl; methoxymethyloxycarbonyl;

$R^2$ is selected from H; methylcarbonyl; tert-butyldimethylsilyl; (C1-C4)alkyl, which can be linear or branched, and which can optionally be substituted with $CH_3O-$, $CH_3S-$; oxacyclohexyl; allyl; tert-butyldiphenylsilyl; tert-butylcarbonyl; phenylcarbonyl; nitrobenzyl; benzyloxymethyl, which can optionally be substituted with $CH_3O-$, $-NO_2$; fluorenylmethyloxycarbonyl; trichlorocarbonyl; trifluorocarbonyl; benzyl; tosyl; mesyl; phenylsulfonyl; allylsulphonyl; ethoxycarbonyl; 2,2,2-trichloroethyloxycarbonyl; methoxycarbonyl; methoxymethyloxycarbonyl;

$M^{3+}$ is a metal cation selected from the group consisting of $In^{3+}$, $Ga^{3+}$, trivalent cations of rare earth elements, selected from lanthanide(III) cations, Y(III) and Sc(III), preferably the metal cation is selected from $Gd^{3+}$ and $Lu^{3+}$;

with the proviso that where $R^1$ is bound to nitrogen, then $R^1$ is not COOH:

with the proviso that where $R^1$ is bound to —CH—, then $R^1$ is independently H or COOH; and with the proviso that one $R^1$ is COOH, and one —CH—$R^1$ group is —$CH_2$—.

The coordination compound according to the present invention thus contains the cyclen based compound of the general formula (I), according to the present invention, coordinated to a metal cation selected from the group consisting of $In^{3+}$, $Ga^{3+}$, trivalent cations of rare earth elements, selected from lanthanide(II) cations, Y(III) and Sc(III), preferably the metal cation is selected from $Gd^{3+}$ and $Lu^{3+}$. The metal ion is coordinated to all four nitrogens of the cyclen moiety, to the three acetate arms of the cyclen moiety and to the carboxylic or —$OR^2$ group present on the proline arm. The metal ion can be in a form of any isotope, including radioisotopes, such as $^{44}Sc$, $^{86}Y$, $^{177}Lu$, $^{161}Tb$, $^{90}Y$.

Another object of the present invention is a peptide, having its chain length of from 2 to 20 amino acids, preferably from 2 to 10 amino acids, more preferably from 3 to 5 amino acids, wherein at least one amino acid is replaced by the cyclen based compound of the general formula (I), according to the present invention, and/or by the coordination compound according to the present invention. The replaced amino acid can be either a terminal amino acid or the replaced amino acid can be non-terminal (any amino acid within the peptide can be replaced).

In one embodiment, the peptide contains at least two coordination compounds according to the present invention, wherein the at least two of the coordination compounds contain different metal ions. Such peptides can be used for combined therapies, using different metal chelates, such as MRI/PET contrast agents in diagnostics, which use $^{44}$Sc or $^{86}$Y as radionuclides, and $Gd^{3+}$ for MRI. More preferably, the peptide contains the following metal complex combinations; Gd and Lu, Gd and Tb, Gd and Y, Tb and Y, Tb and Lu, Lu and Y.

Another object of the present invention is a pharmaceutical preparation, which contains at least one coordination compound according to the present invention, or at least one peptide according to the present invention, and a pharmaceutically acceptable auxiliary substance. The dosage form of the pharmaceutical preparation is a form for administration by injection, most often as a bolus or as an infusion, preferably intravenously. Suitable pharmaceutically acceptable auxiliary substances are preferably selected from the group containing solvents (especially aqueous or saline solution), buffers (especially phosphate buffer, HEPES=2-[4-(2-hydroxyethyl)piperazine-1-yl]ethanesulfonic acid), ionization additives, antioxidants, antimicrobial additives. A person skilled in the art would be able, without exerting inventive activity, to determine which adjuvans to choose.

A further object of the present invention is the use of the coordination compound according to the present invention and/or of the peptide according to the present invention and/or of the pharmaceutical preparation according to the present invention, in medicine.

Another object of the present invention is the use of the coordination compound according to the present invention and/or of the peptide according to the present invention and/or of the pharmaceutical preparation according to the present invention as MRI contrast agent and/or PET contrast agent and/or MRI-SPECT contrast agent and/or combined MRI contrast agent and radiopharmaceutical agent for therapy and/or combined PET contrast agent and radiopharmaceutical agent for radiotherapy.

EXAMPLES

The numerical values of chemical shift in NMR spectra are given in ppm. Notation used in the NMR spectra: s (singlet), d (dublet), t (triplet), m (multiplet), bs (broad singlet). The reference was set to the following values: $^1$H: 7.26 ppm ($CDCl_3$); 1.94 ($CD_3CN$); 2.5 ppm (DMSO-d6). $^{13}$C: 77.16 ppm ($CDCl_3$); 118.26 ppm ($CD_3CN$); 39.52 ppm (DMSO-d6).

List of Abbreviations

Bn (benzyl); Cbz (benzyloxycarbonyl); DCM (dichloromethane); DIPEA (N,N-diisopropylethylamine); DMF (dimethylformamide); ESI (electrospray ionization); FA (formic acid); Fmoc (fluorenylmethyloxycarbonyl); HATU (1-[Bis(dimethylamino)methylene]-1H-1,2,3-triazolo[4,5-b]pyridinium 3-oxid hexafluorophosphate); HPLC (high performance liquid chromatography); HRMS (high resolution mass spectrometry); ICP-AES (inductively coupled plasma-atomic emission spectroscopy); LC-MS (liquid chromatography-mass spectrometry); MOPS (3-morpholinopropane-1-sulfonic acid); NMP (N-Methyl-2-pyrrolidone); TFA (trifluoroacetic acid); UV (ultraviolet).

I. Synthesis of Compounds

Example 1

Preparation of dibenzyl (1R,2S,5S)-6-oxa-3-azabicyclo[3.1.0]hexane-2,3-dicarboxylate (1a) and dibenzyl (1S,2S,5R)-6-oxa-3-azabicyclo[3.1.0]hexane-2,3-dicarboxylate (1b)

Dibenzyl (S)-2,5-dihydro-1H-pyrrole-1,2-dicarboxylate (6.80 g, 20.16 mmol) was dissolved in chloroform (200 mL) at room temperature and m-chloroperoxybenzoic acid (77%, 6.78 g, 30.26 mmol) was added. The reaction mixture was heated up to 85° C. on oil bath for 24 h. The volume of the solvent was reduced on rotary evaporator. DCM (70 mL) was added to the precipitate and reaction mixture was put into freezer. After 24 h the white precipitate was removed by filtration, the filtrate was evaporated and the residue was purified by FLASH chromatography on 120 g silica gel column using petroleum ether:ethyl acetate gradient from (100:0) to (60:40). The chromatography provided separation of the two isomers. Fractions containing pure compounds were evaporated, giving 3.3 g of 1a as transparent oil (9.32 mmol, 46% yield) and 1.5 g of 1b as white solid (4.23 mmol, 21% yield).

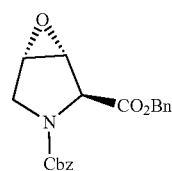

1a $^1$H NMR ($CDCl_3$, 25° C., 400 MHz): $\delta_H$ 3.56 (ddd, 1H); $\delta_H$ 3.68 (ddd, 1H); $\delta_H$ 3.77 (d, 1H); 3.91-3.99 (m, 1H); 4.74 (d, 1H); 5.05-5.28 (m, 4H); 7.23-7.40 (arom., in, 10H).

HRMS (ESI) m/z: [(M+Na)$^+$] ($C_{20}H_{19}O_5NNa$) calculated: 376.11554. found: 376.11523.

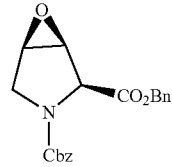

1b $^1$H NMR ($CDCl_3$, 25° C., 400 MHz): $\delta_H$ 3.61 (ddd, 1H); $\delta_H$ 3.77-3.81 (m, 1H); $\delta_H$ 3.79 (d, 1H); 3.88-3.98 (m, 1H); 4.49 (dd, 1H); 4.94-5.31 (m, 4H); 7.21-7.39 (arom., m, 10H).

HRMS (ESI) m/z: [(M+Na)$^+$] ($C_{20}H_{19}O_5NNa$) calculated: 376.11554. found: 376.11514.

Preparation of dibenzyl (2S,3S,4S)-3-(1,4,7,10-tetraazacyclododecan-1-yl)-4-hydroxypyrrolidine-1,2-dicarboxylate (1c) and dibenzyl (2S,3S,4R)-4-(1,4,7,10-tetraazacyclododecan-1-yl)-3-hydroxypyrrolidine-1,2-dicarboxylate (1d)

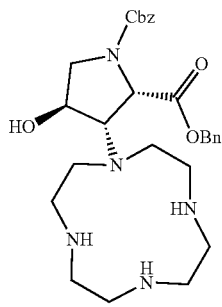

1c

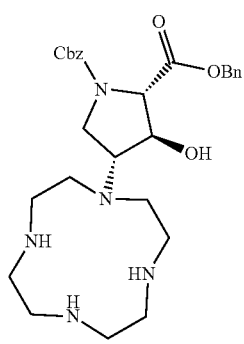

1d

Dibenzyl (1R,2S,5S)-6-oxa-3-azabicyclo[3.1.0]hexane-2,3-dicarboxylate (1a) (2 g, 5.66 mmol) and 1,4,7,10-tetraazacyclododecane (3.9 g, 22.64 mmol) in 117 mL of t-BuOH were placed into a 250 mL round bottom flask and the mixture was stirred for 24 hours and heated under reflux. After cooling to room temperature the reaction mixture was neutralized with TFA (3 mL, 39.20 mmol). Reaction mixture was concentrated on rotary evaporator. Resulting oil was purified on reversed-phase flash chromatography (C18 column, acetonitrile/water gradient with 0.1% trifluoroacetic acid in the mobile phase). Fractions containing mixture of the two products were pooled, evaporated and dried in high vacuum. The residue was dissolved in water (5 ml) and lyophilized giving 2.3 g of the product as a brown solid in form of TFA salt (30.40 mmol, 54% yield relative to 1a). Based on $^1$H NMR the product contained mixture of isomers (2S,3S,4S) (1c)/(2S,3S,4R) (1d) in ratio 9/1.

HRMS (ESI) m/z: [(M+H)$^+$] ($C_{28}H_{40}O_5N_5$) calculated: 526.30240. found: 526.30100.

Elem. analysis: M.2.1TFA.0.5H$_2$O, calculated: C; (50.0), H; (5.5), N; (9.0), F; (15.5). found: C; (49.5), H; (5.1), N; (8.8), F; (16.3).

Preparation of dibenzyl (2S,3S,4S)-4-hydroxy-3-(4,7,10-tris(2-(tert-butoxy)-2-oxoethyl)-1,4,7,10-tetraazacyclododecan-1-yl)pyrrolidine-1,2-dicarboxylate (1e) and dibenzyl (2S,3S,4R)-3-hydroxy-4-(4,7,10-tris(2-(tert-butoxy)-2-oxyethyl)-1,4,7,10-tetraazacyclododecan-1-yl)pyrrolidine-1,2-dicarboxylate (1f)

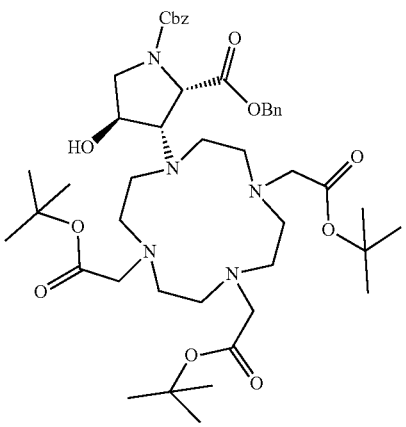

1e

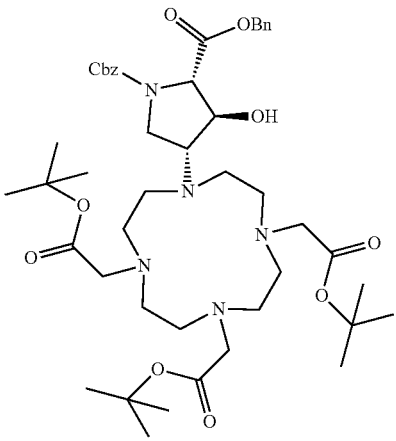

1f

A mixture of isomers 1c and 1d in ratio 9/1 (1 g, 1.32 mmol), t-Butyl bromoacetate (799 uL, 5.41 mmol), anhydrous cesium carbonate (2.58 g, 7.92 mmol) and acetonitrile (50 mL) were placed into a 100 mL round bottom flask and the mixture was stirred for 1 hour at room temperature. The solids were filtered off and the filtrate was concentrated on rotary evaporator. Resulting oil was purified on reversed-phase flash chromatography (C18 column, acetonitrile/water gradient with 0.1% trifluoroacetic acid in the mobile phase). Fractions containing mixture of the two products were pooled, evaporated and dried in high vacuum giving 1.19 g of yellow glass-like solid. The product contained mixture of isomers (2S,3S,4S) (1e)/(2S,3S,4R) (1f) in ratio 9/1 (based on LC-MS) in the form of salt with TFA (83% yield, assuming composition M.2TFA).

HRMS (ESI) m/z: [(M+H)$^+$] ($C_{46}H_{70}O_{11}N_5$) calculated: 868.50663. found: 868.50631.

Preparation of (2S,3S,4S)-4-hydroxy-3-(4,7,1-tris(2-(tert-butoxy)-2-oxoethyl)-1,4,7,10-tetraazacyclododecan-1-yl)pyrrolidine-2-carboxylic acid (1g) and (2S,3R,4R)-3-hydroxy-4-(4,7,10-tris(2-(tert-butoxy)-2-oxoethyl)-1,4,7,10-tetraazacyclododecan-1-yl)pyrrolidine-2-carboxylic acid (1h)

A mixture of isomers 1e and 1f in ratio 9/1 (500 mg, 0.46 mmol) in 100 mL round bottom flask with septum

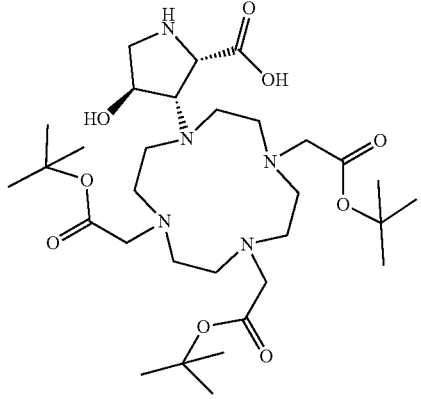

1g

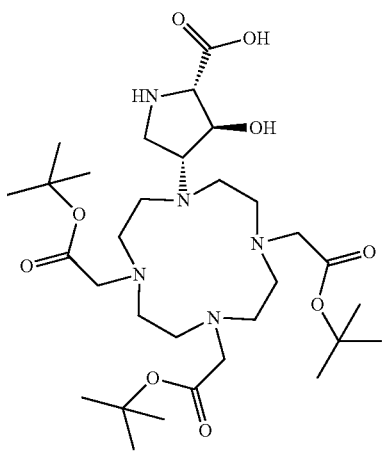

1h was dissolved in MeOH (32 mL). 10% Pd/C (41 mg, 0.038 mmol) was added to the reaction mixture. The mixture was stirred for 30 minutes under argon atmosphere at room temperature after which the reaction mixture was filtered through celite pad. The filtrate was concentrated on rotary evaporator and dried in high vacuum. The residue was dissolved in water (2 mL) and lyophilized to give 390 mg of white solid. The product contained mixture of isomers (2S,3S,4S) (1g)/(2S,3R,4R) (1h) in ratio 9/1 in the form of salt with TFA (97% yield, assuming composition M.2TFA). HRMS (ESI) m/z: [(M+H)$^+$] ($C_{31}H_{58}O_9N_5$) calculated: 644.42290. found: 644.42270.

Example 2: Preparation of (2S,3S,4S)-1-(((9H-fluoren-9-yl)methoxy)carbonyl)-4-hydroxy-3-(4,7,10-tris(2-(tert-butoxy)-2-oxoethyl)-1,4,7,10-tetraazacyclododecan-1-yl)pyrrolidine-2-carboxylic acid (2)

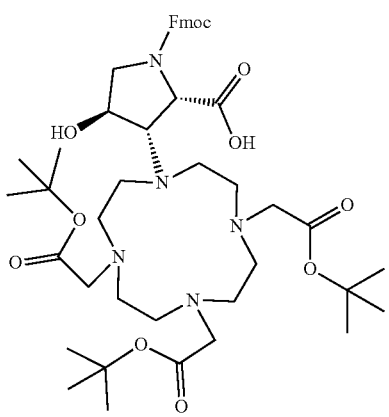

A mixture of isomers 1g and 1h in ratio 9/1 (390 mg, 0.45 mmol) was dissolved in mixture of acetonitrile (23.4 mL) and borate buffer (22 mL, 0.2 M, pH=9). Fmoc chloride (0.114 g, 0.44 mmol) was added to reaction mixture and reaction mixture was stirred for 30 minutes at room temperature. The reaction mixture was purified on reversed-phase flash chromatography (C18 column, acetonitrile/water gradient with 0.1% trifluoroacetic acid in the mobile phase). Chromatography provided separation of (2S,3S,4S) and (2S,3S,4R). Fractions containing pure isomer (2S,3S,4S) were pooled, evaporated and dried in high vacuum giving 286 mg of product as white crystalline solid in the form of salt with TFA (58% yield, assuming composition M.2TFA).
HRMS (ESI) m/z: [(M−H)$^-$] ($C_{46}H_{66}O_{11}N_5$) calculated: 864.47643. found: 864.47490.

Example 3: Preparation of 2,2',2''-(10-((2S,3S,4S)-1-(2-(9H-fluoren-9-yl)acetoxy)-2-carboxy-4-hydroxypyrrolidin-3-yl-1,4,7,10-tetraazacyclododecane-1,4,7-triyl)triacetic acid (3)

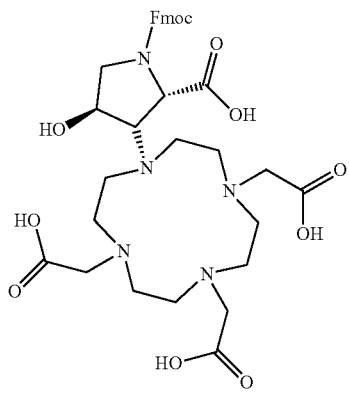

Compound 2 prepared in Example 2 (286 mg, 0.26 mmol) was dissolved in TFA (5 mL, 65.34 mmol). The mixture was stirred for 30 minutes at 70° C. after which the reaction mixture was concentrated on rotary evaporator and dried in high vacuum. The residue was dissolved in water (2 ml) and lyophilized to give 200 mg of brown solid in the form of salt with TFA (95% yield, assuming composition M.2TFA).

HRMS (ESI) m/z: [(M+H)+] ($C_{34}H_{44}O_{11}N_5$) calculated: 698.30318. found: 698.30337.

$^1$H NMR (DMSO-$d_6$, 500 MHz): $\delta_H$ 2.67-3.29 (cycle+proline arm, m, 17H); 3.42-3.93 (proline arm+acetates, m, 8H); 4.07-4.33 (proline arm+fmoc, m, 5H); 7.29-7.37 (arom., m, 2H); 7.40-7.45 (arom., m, 2H); 7.62-7.67 (arom., m, 2H); 7.87-7.92 (arom., m, 2H); $^{13}$C{$^1$H} NMR (DMSO-$d_6$, 125 MHz): 45.68-54.03 (cycle+carboxylates, m); 46.82, 46.89 (fmoc, s); 50.91, 51.4 (proline arm, s); 57.01, 56.84 (proline arm, s); 66.89, 67.33 (proline arm, s); 69.13, 69.24 (proline arm, s); 70.20, 71.43 (proline arm, s); 120.33-120.44 (arom., m); 125.30, 125.38, 125.45, 125.54 (arom., s); 127.35-127.43 (arom., m); 127.97 (arom., s); 140.86, 140.92, 140.99, 141.02 (arom., s); 143.85, 143.88, 143.95, 143.99 (arom., s); 153.84, 154.05 (N—COO); 170.25, 172.11 (CH2-COO); 173.48, 173.73 (CO).

Example 4: Preparation of Gd(III) Complex of 2,2',2''-(10-((2S,3S,4S)-1-(2-(9H-fluoren-9-yl)acetoxy)-2-carboxy-4-hydroxypyrrolidin-3-yl)-1,4,7,10-tetraazacyclododecane-1,4,7-triyl)triacetic acid (Gd-3)

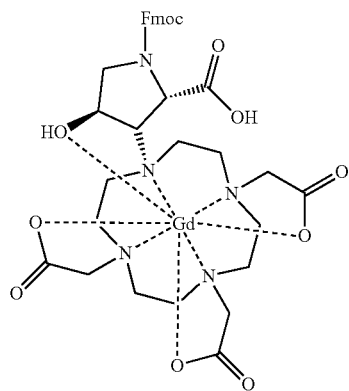

Fmoc Compound 3 prepared in Example 3 (200 mg, 0.22 mmol) was dissolved in a mixture of methanol (20 mL) and water (20 mL). Aqueous solution of GdCl3 OH 25 (2.167 mL, 0.1 M) and aqueous solution of N-methyl morpholine (15.166 mL, 0.1 M) was added to the reaction mixture. The reaction mixture was stirred for 1 hour at room temperature. Then, reaction mixture was concentrated on rotary evaporator. The residue was purified on reversed-phase flash chromatography (C18 column, acetonitrile/water gradient). Fractions containing pure product were pooled, evaporated and dried in high vacuum. The residue was dissolved in water (2 ml) and lyophilized giving 170 mg of the product as a white solid (87% yield relative to 3).

HRMS (ESI) m/z: [(M−H)−] ($C_{34}H_{39}O_{11}N_5Gd$) calculated: 851.18926. found: 851.18776.

Elem. analysis: M.2H2O, calculated: C; (46.0), H; (5.0), N; (7.9), Gd; (17.7). found: C; (46.5), H; (5.5), N; (8.2), Gd; (14.8).

Example 5: Preparation of Lu(III) Complex of 2,2',2''-(10-((2S,3S,4S)-1-(2-(9H-fluoren-9-yl)acetoxy)-2-carboxy-4-hydroxypyrrolidin-3-yl)-1,4,7,10-tetraazacyclododecane-1,4,7-triyl)triacetic acid (Lu-3)

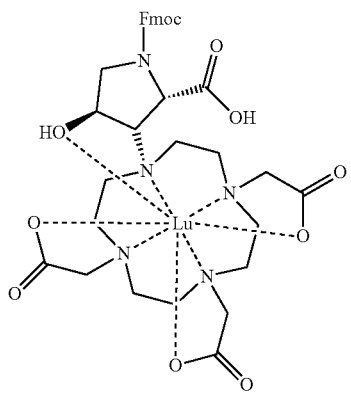

According to procedure in Example 4, reaction of compound 3 (83 mg, 0.083 mmol), aqueous solution of LuCl3 (838 uL, 0.1 M) and aqueous solution of N—OH methyl morpholine (5.867 mL, 0.1 M) analogously provided 31 mg of the product as a white solid (43% yield relative to 3).

HRMS (ESI) m/z: [(M+H)+] ($C_{34}H_{41}O_{11}N_5Lu$) calculated: 870.22048. found: 870.21970.

Example 6: Preparation of Gd(III) Complex of 2,2',2''-(10-((2S,3S,4S)-2-carboxy-4-hydroxypyrrolidin-3-yl)-1,4,7,10-tetraazacyclododecane-1,4,7-triyl)triacetic acid (Gd-6)

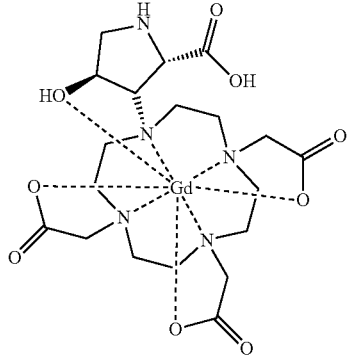

Compound Gd-3 (7 mg, 0.008 mmol) was dissolved in water (0.5 mL). Aqueous solution of LiOH (0.5 mL, 1 M) was added. The reaction mixture was stirred for 1 hour at room temperature. Then, reaction mixture was concentrated on rotary evaporator. The residue was purified on reversed-phase flash chromatography (C18 column, acetonitrile/water gradient with 0.1% formic acid in the mobile phase). Fractions were pooled, evaporated and dried in high vacuum giving 3 mg of the product as a white solid. The product was in the form of salt with formic acid (54% yield, assuming composition M.1FA).

LCMS (ESI) m/z: [(M+H)+] ($C_{19}H_{31}O_9N_5$) calculated: 631.1. found: 631.4.

Example 7: Preparation of dibenzyl (2S,3S,4S)-4-acetoxy-3-(4,7,10-tris(2-(tert-butoxy)-2-oxoethyl)-1,4,7,10-tetraazacyclododecan-1-yl)pyrrolidine-1,2-dicarboxylate (7a) and dibenzyl (2S,3S,4R)-3-acetoxy-4-(4,7,10-tris(2-(tert-butoxy)-2-oxoethyl)-1,4,7,10-tetraazacyclododecan-1-yl)pyrrolidine-1,2-dicarboxylate (7b)

Preparation of (2S,3S,4S)-4-acetoxy-3-(4,7,10-tris(2-(tert-butoxy)-2-oxoethyl)-1,4,7,10-tetraazacyclododecan-1-yl)pyrrolidine-2-carboxylic acid (7c) and (2S,3R,4R)-3-acetoxy-4-(4,7,10-tris(2-(tert-butoxy)-2-oxoethyl)-1,4,7,10-tetraazacyclododecan-1-yl)pyrrolidine-2-carboxylic acid (7d)

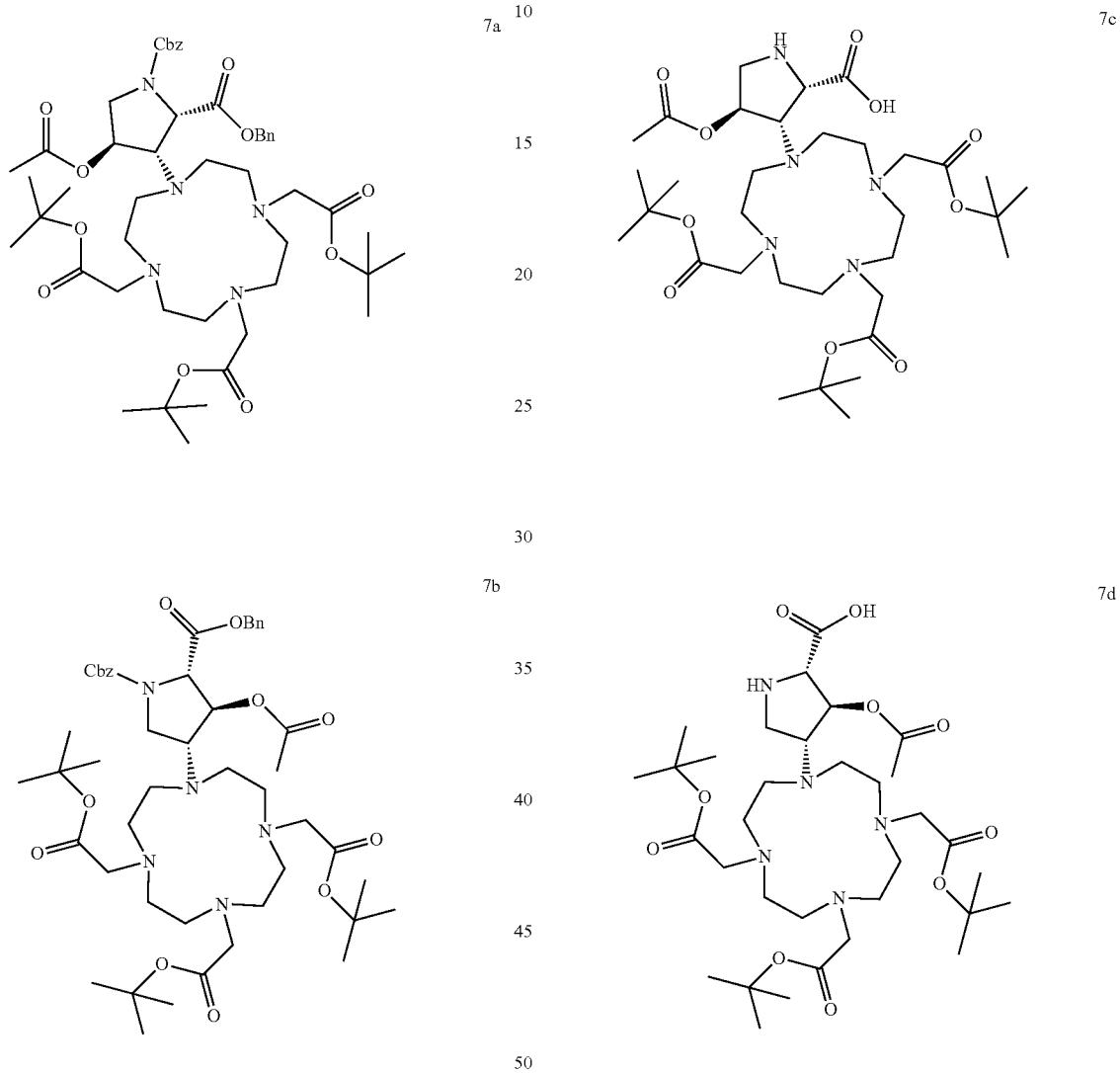

A mixture of isomers 1e and 1f in ratio 9/1 prepared in Example 1 (100 mg, 0.091 mmol), acetic anhydride (15 uL, 0.015 mmol), triethyl amine (64 uL, 0.046 mmol) and dimethyl aminopyridine (0.2 mg, 0.0002 mmol) was dissolved in acetonitrile (50 mL). The mixture was stirred overnight at room temperature after which the reaction mixture was concentrated on rotary evaporator and dried in high vacuum. Resulting oil was purified on reversed-phase flash chromatography (C18 column, acetonitrile/water gradient with 0.1% trifluoroacetic acid in the mobile phase). Fractions containing mixture of the two products were pooled, evaporated and dried in high vacuum giving 103 mg of colorless solid. The product contained mixture of isomers (2S,3S,4S) (7a)/(2S,3S,4R) (7b) in ratio 9/1 in the form of salt with TFA (99% yield, assuming composition M.2TFA).

HRMS (ESI) m/z: [(M+H)$^+$] ($C_{48}H_{72}O_{12}N_5$) calculated: 910.51720. found: 910.51711.

The procedure was analogous to preparation of compounds 1g and 1h in Example 1. Reaction of the mixture of isomers 7a and 7b in ratio 9/1 (93 mg, 0.082 mmol), 10% Pd/C (8 mg, 0.008 mmol) in MeOH (32 mL) gave analogously 65.5 mg of the product as a white solid. The product contained mixture of isomers (2S,3S,4S) (7a)/(2S,3R,4R) (7b) in ratio 9/1 in the form of salt with TFA (88% yield, assuming composition M.2TFA).

LCMS (ESI) m/z: [(M+H)$^+$] ($C_{33}H_{60}O_{10}N_5$) calculated: 686.43. found: 686.6.

Example 8: Preparation of (2S,3S,4S)-1-(((9H-fluoren-9-yl)methoxy)carbonyl)-4-acetoxy-3-(4,7,10-tris(2-(tert-butoxy)-2-oxoethyl)-1,4,7,10-tetraazacyclododecan-1-yl)pyrrolidine-2-carboxylic acid (8)

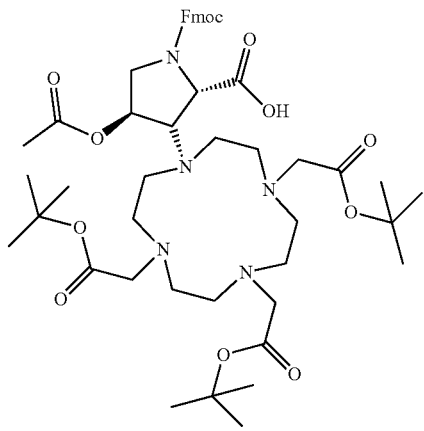

According to procedure in Example 2, reaction of a mixture of isomers 7a and 7b in ratio 9/1 (60 mg), Fmoc chloride (18 mg, 0.07 mmol) in acetonitrile (3.6 mL) and borate buffer (3.4, 0.2 M, pH=9) was carried out. Chromatography analogously to Example 2 provided separation of the isomers (2S,3S,4S) and (2S,3S,4R), yielding 41 mg of pure isomer (2S,3S,4S) as a colorless solid in the form of salt with TFA (55% yield, assuming composition M.2TFA).

LCMS (ESI) m/z: [(M+H)$^+$] ($C_{48}H_{70}O_{12}N_5$) calculated: 908.5. found: 908.5.

Example 9: Preparation of 2,2',2''-(10-((2S,3S,4S)-1-(((9H-fluoren-9-yl)methoxy)carbonyl)-4-acetoxy-2-carboxypyrrolidin-3-yl)-1,4,7,10-tetraazacyclododecane-1,4,7-triyl)triacetic acid (9)

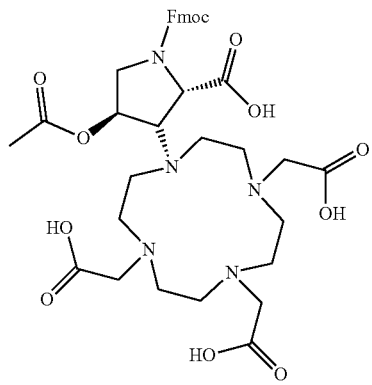

According to procedure in Example 3, reaction of starting compound 8 prepared in Example 8 (41 mg) in TFA (2 mL, 26.14 mmol) gave analogously 35 mg of the product as a brownish solid in the form of salt with TFA (100% yield, assuming composition M.2TFA).

HRMS (ESI) m/z: [(M+H)$^+$] ($C_{36}H_{46}O_{12}N_5$) calculated: 740.31375. found: 740.31301.

Example 10: Preparation of Gd(III) Complex of 2,2',2''-(10-((2S,3S,4S)-1-(((9H-fluoren-9-yl)methoxy)carbonyl)-4-acetoxy-2-carboxypyrrolidin-3-yl)-1,4,7,10-tetraazacyclododecane-1,4,7-triyl)triacetic acid (Gd-9)

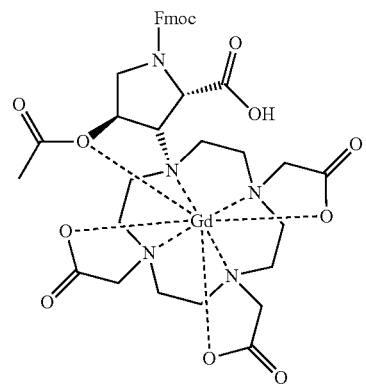

According to procedure in Example 4, reaction of starting compound 9 prepared in Example 9 (25 mg, 0.026 mmol) in methanol (2.5 mL) and water (2.5 mL) with aqueous solution of $GdCl_3$ (263 uL, 0.1 M) and aqueous solution of N-methyl morpholine (1.842 mL, 0.1 M) gave analogously 14 mg of the product as a white solid (57% yield relative to compound 9).

HRMS (ESI) m/z: [(M–H)$^-$] ($C_{36}H_{41}O_{12}N_5Gd$) calculated: 893.19982. found: 893.19873.

Elem. analysis: M.3H$_2$O, calculated: C; (45.6), H; (5.1), N; (7.4), Gd; (16.6), found: C; (46.0), H; (5.4), N; (7.6), Gd; (13.7).

Example 11: Preparation of dibenzyl (2S,3S,4S)-4-hydroxy-3-(4,7,10-tris(2-methoxy-2-oxoethyl)-1,4,7,10-tetraazacyclododecan-1-yl)pyrrolidine-1,2-dicarboxylate (11a) and dibenzyl (2S,3S,4R)-3-hydroxy-4-(4,7,10-tris(2-methoxy-2-oxoethyl)-1,4,7,10-tetraazacyclododecan-1-yl)pyrrolidine-1,2-dicarboxylate 11a

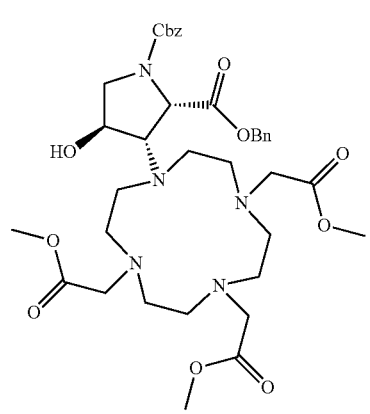

11b

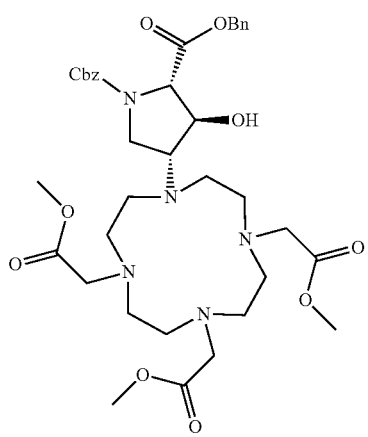

A mixture of isomers 1c and 1d in ratio 9/1 (200 mg, 0.26 mmol), methyl bromoacetate (143 uL, 1.23 mmol), anhydrous cesium carbonate (516 mg, 1.59 mmol) and acetonitrile (10 mL) were placed into a 100 mL round bottom flask and the mixture was stirred for 2 h at room temperature. The solids were filtered off and the filtrate was concentrated on rotary evaporator. Resulting oil was purified on reversed-phase flash chromatography (C18 column, acetonitrile/water gradient with 0.1% trifluoroacetic acid in the mobile phase). Fractions containing mixture of the two products were pooled, evaporated and dried in high vacuum giving 197.5 mg of a colourless solid. The product contained mixture of isomers (2S,3S,4S) (11a)/(2S,3S,4R) (11b) isomers in ratio 9/1 in the form of salt with TFA (77% yield, assuming composition M.2TFA).

HRMS (ESI) m/z: [(M+H)$^+$] ($C_{37}H_{52}O_{11}N_5$) calculated: 742.36578. found: 742.36566.

Preparation of dibenzyl (2S,3S,4S)-4-acetoxy-3-(4, 7,10-tris(2-methoxy-2-oxoethyl)-1,4,7,10-tetraazacyclododecan-1-yl)pyrrolidine-1,2-dicarboxylate (11c) and dibenzyl (2S,3S,4R)-3-acetoxy-4-(4,7,10-tris(2-methoxy-2-oxoethyl)-1,4,7,10-tetraazacyclododecan-1-yl)pyrrolidine-1,2-dicarboxylate 11d

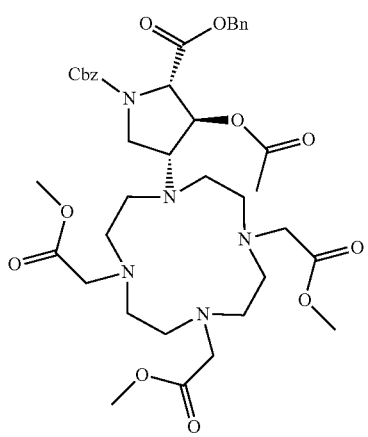

The reaction was carried out according to procedure in Example 7 for preparation of 7a and 7b. Analogously, a mixture of isomers 11a and 11b in ratio 9/1 prepared in Example 11 (158 mg, 0.16 mmol), acetic anhydride (31.5 uL, 0.034 mmol), triethyl amine (64 uL, 0.081 mmol) and dimethyl aminopyridine (0.3 mg, 0.0003 mmol) was dissolved in acetonitrile (7.563 mL) gave analogously 100 mg of the product as a colorless solid. The product contained mixture of isomers (2S,3S,4S) (11c)/(2S,3S,4R) (11d) in ratio 9/1 in the form of salt with TFA (81% yield, assuming composition M.2TFA).

HRMS (ESI) m/z: [(M+H)$^+$] ($C_{39}H_{54}O_{12}N_5$) calculated: 784.37635. found: 784.37567.

Preparation of (2S,3S,4S)-4-acetoxy-3-(4,7,10-tris(2-methoxy-2-oxoethyl)-1,4,7,10-tetraazacyclododecan-1-yl)pyrrolidine-2-carboxylic acid (11e) and (2S,3R,4R)-3-acetoxy-4-(4,7,10-tris(2-methoxy-2-oxoethyl)-1,4,7,10-tetraazacyclododecan-1-yl)pyrrolidine-2-carboxylic acid (11f)

11c

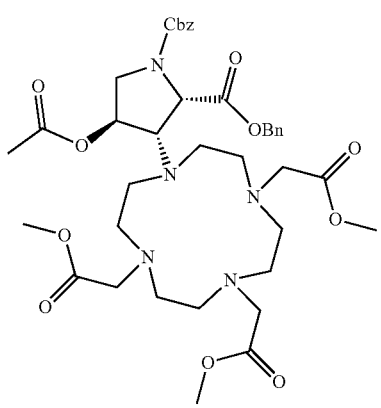

11e

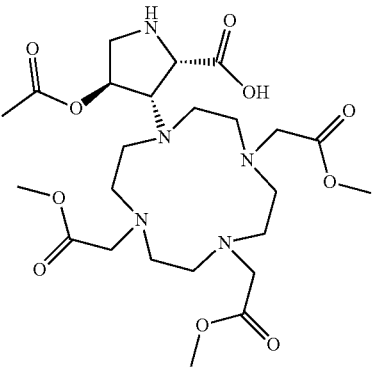

-continued

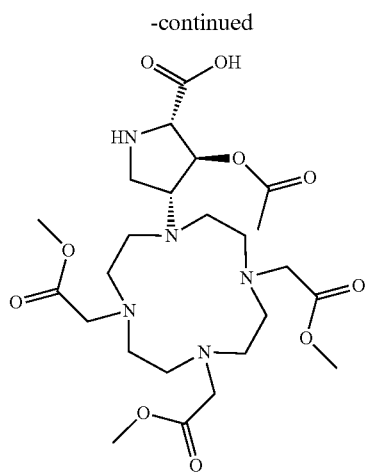

11f

The procedure was analogous to preparation of compounds 1g and 1h in Example 1. Reaction of the mixture of isomers 11c and 11d in ratio 9/1 (100 mg, 0.13 mmol), 10% Pd/C (11 mg, 0.011 mmol) in MeOH (10 mL) gave analogously 76 mg of the product as a colorless solid. The product contained mixture of isomers (2S,3S,4S) (11e)/(2S,3R,4R) (11f) in ratio 9/1 in the form of salt with TFA (74% yield, assuming composition M.2TFA).

HRMS (ESI) m/z: [(M+H)$^+$] ($C_{24}H_{42}O_{10}N_5$) calculated: 560.29262. found: 560.29214.

Example 12: Preparation of (2S,3S,4S)-1-(((9H-fluoren-9-yl)methoxy)carbonyl)-4-acetoxy-3-(4,7,10-tris(2-methoxy-2-oxoethyl)-1,4,7,10-tetraazacyclododecan-1-yl)pyrrolidine-2-carboxylic acid (12)

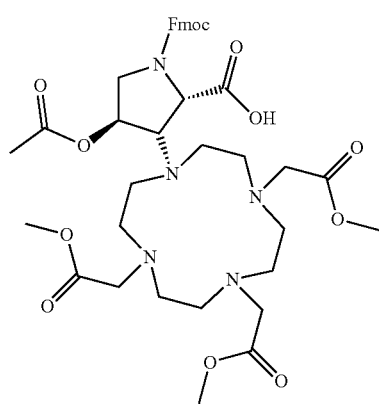

According to procedure in Example 2, reaction of a mixture of isomers 11e and 11f in ratio 9/1 (70 mg, 0.089 mmol), Fmoc chloride (18.5 mg, 0.072 mmol) in acetonitrile (4.3 mL) and borate buffer (4 mL, 0.2M, pH=9) was carried out. Chromatography analogously to Example 2 provided separation of the isomers (2S,3S,4S) and (2S,3S,4R), yielding 74 mg of pure isomer (2S,3S,4S) as a colorless solid in the form of salt with TFA (82% yield, assuming composition M.2TFA).

HRMS (ESI) m/z: [(M+H)$^+$] ($C_{39}H_{52}O_{12}N_5$) calculated: 782.36070. found: 782.35995.

$^1$H NMR (CD$_3$CN, 500 MHz): $\delta_H$ 1.99, 2.02 (acetate, bs, 3H); 3.71 (methyl ester, s, 3H); 3.77 (Methyl ester, m, 6H); 2.66-4.12 (proline arm, cycle, cycle carboxylate, m, 25H); 4.13-4.32 (proline arm, fmoc, m, 2H); 4.37-4.50 (fmoc, m, 2H); 4.96, 5.05 (proline arm, bs, 1H) 7.33-7.37 (arom., m, 2H); 7.41-7.44 (arom., m, 2H); 7.61-7.67 (arom., m, 2H); 7.82-7.86 (arom., m, 2H); $^{13}$C{$^1$H} NMR (CD$_3$CN, 125 MHz): 21.31 (acetate, s); 48.24 (fmoc, s); 52.99, 53.62 (methyl ester, s); 46.89-55.14 (proline arm, cycle, carboxylates, m); 58.77, 59.93 (proline arm, s); 68.43 (fmoc, s); 69.05, 70.43 (proline arm, s); 74.03 (proline arm, s); 121.12, 126.22, 128.30, 128.90 (arom., s); 142.25-142.41 (arom., m); 145.06-145.28 (arom., m); 154.69, 155.47 (N—COO); 169.48-172.59 (COO, m).

Example 13: Preparation of dibenzyl (2S,3S,4S)-4-((tert-butyldimethylsilyl)oxy)-3-(4,7,10-tris(2-(tert-butoxy)-2-oxoethyl)-1,4,7,10-tetraazacyclododecan-1-yl)pyrrolidine-1,2-dicarboxylate (13a) and dibenzyl (2S,3S,4R)-3-((tert-butyldimethylsilyl) oxy)-4-(4,7,10-tris(2-(tert-butoxy)-2-oxoethyl)-1,4,7,10-tetraazacyclododecan-1-yl)pyrrolidine-1,2-dicarboxylate (13b)

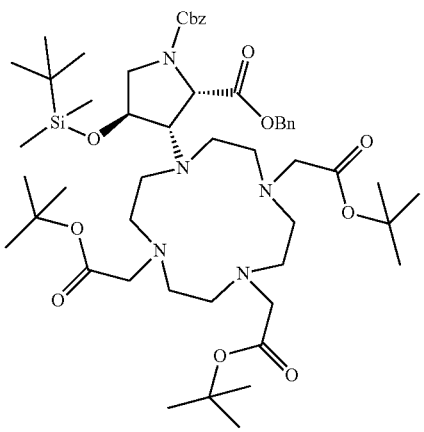

13a

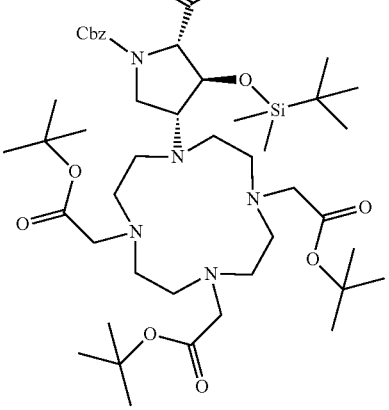

13b

A mixture of isomers 1e and 1f in ratio 9/1 prepared in Example 1 (24 mg, 0.022 mmol), t-Butyl dimethyl silyl chloride (62.5 mg, 0.43 mmol), 1,8-diazabicyklo (5.4.0) undec-7-en (62.5 mg, 0.43 mmol) and dimethyl aminopyridine (62.5 mg, 0.43 mmol) was dissolved in acetonitrile (1 mL). The mixture was stirred for 7.5 hours at 70° C., after which the reaction mixture was diluted with methanolic solution of triethylammonium acetate (1 mL, 1M). Reaction mixture was purified on preparative HPLC (C18 column, acetonitrile/water gradient with 0.1% acetic acid in the mobile phase). Fractions mixture of the two products were pooled, evaporated and dried in high vacuum giving 7 mg of the product as a colorless solid. The product contained mixture of isomers (2S,3S,4S) (13a)/(2S,3S,4R) (13b) in ratio 9/1 in the form of salt with acetic acid (29% yield, assuming composition M.2AcOH).

LCMS (ESI) m/z: [(M+H)$^+$] ($C_{52}H_{84}O_{11}N_5Si$) calculated: 982.6. found: 982.7.

Preparation of (2S,3S,4S)-4((tert-butyldimethylsilyl)oxy)-3-(4,7,10-tris(2-(tert-butoxy)-2-oxoethyl)-1,4,7,10-tetraazacyclododecan-1-yl)pyrrolidine-2-carboxylic acid (13c) and (2S,3R,4R)-3-((tert-butyldimethylsilyl)oxy)-4(4,7,10-tris(2-(tert-butoxy)-2-oxoethyl)-1,4,7,10-tetraazacyclododecan-1-yl)pyrrolidine-2-carboxylic acid (13d)

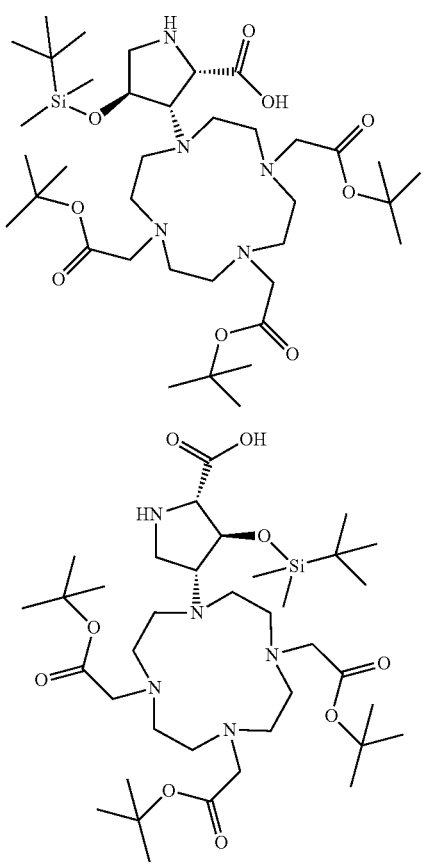

The procedure was analogous to preparation of compounds 1g and 1h in Example 1. Reaction of the mixture of isomers 13a and 13b in ratio 9/1 (7 mg, 0.006 mmol), 10% Pd/C (11 mg, 0.001 mmol) in MeOH/DCM (1/1) (3 mL) gave analogously 4 mg of the product as a colorless solid. The product contained mixture of isomers (2S,3S,4S) (13c)/13c 13d (2S,3R,4R)(13d) in ratio 9/1 in the form of salt with acetic acid (77% yield, assuming composition M.2AcOH).

LCMS (ESI) m/z: [(M+H)$^+$] ($C_{37}H_{72}O_9N_5Si$) calculated: 758.5. found: 758.5.

Example 14: Preparation of (2S,3S,4S)-1-(((9H-fluoren-9-yl)methoxy)carbonyl)-4-((tert-butyldimethylsilyl)oxy)-3-(4,7,10-tris(2-(tert-butoxy)-2-oxoethyl)-1,4,7,10-tetraazacyclododecan-1-yl)pyrrolidine-2-carboxylic acid (14)

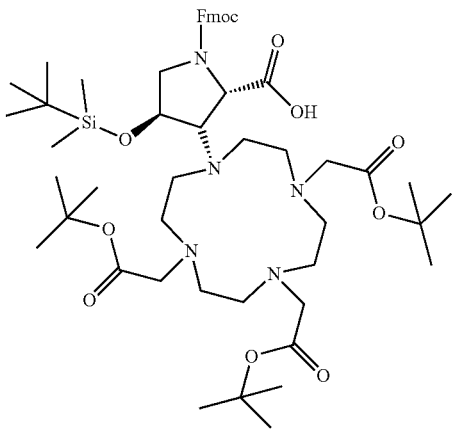

According to procedure in Example 2, reaction of a mixture of isomers 13c and 13d in ratio 9/1 prepared in Example 13 (4 mg, 0.004 mmol), Fmoc chloride (0.8 mg, 0.003 mmol) in acetonitrile (560 uL) and borate buffer (520 uL, 0.2M, pH=9) was carried out. Reaction mixture was purified on preparative HPLC (C18 column, acetonitrile/water gradient with 0.1% acetic acid in the mobile phase). The chromatography provided separation of the isomers (2S,3S,4S) and (2S,3S,4R), yielding 2 mg of pure isomer (2S,3S,4S) as a colorless solid in the form of salt with acetic acid (45% yield, assuming composition M.2AcOH).

LCMS (ESI) m/z: [M+2H$^+$]$^{2+}$ ($C_{52}H_{82}O_{11}N_5Si$) calculated: 490.8. found: 490.9.

Example 15: Preparation of dibenzyl (2R,3S,4S)-3-(1,4,7,10-tetraazacyclododecan-1-yl)-4-hydroxypyrrolidine-1,2-dicarboxylate (15a) and dibenzyl (2R,3S,4R)-4-(1,4,7,10-tetraazacyclododecan-1-yl)-3-hydroxypyrrolidine-1,2-dicarboxylate (15b)

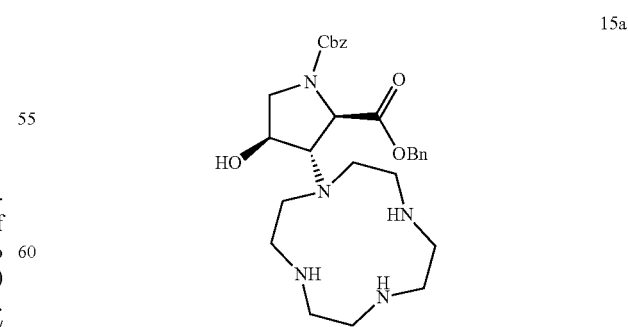

15b

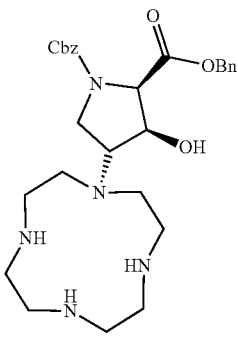

Dibenzyl (1S,2S,5R)-6-oxa-3-azabicyclo[3.1.0]hexane-2,3-dicarboxylate (1b) (500 mg, 1.41 mmol) and 1,4,7,10-tetraazacyclododecane (975 mg, 5.66 mmol) in 29.25 mL of t-BuOH were placed into a 100 mL round bottom flask and the mixture was stirred for 18 hours and heated under reflux. After cooling to room temperature the reaction mixture was neutralized with TFA (600 uL, 7.84 mmol). Reaction mixture was concentrated on rotary evaporator. Resulting oil was purified on reversed-phase flash chromatography (C18 column, acetonitrile/water gradient with 0.1% trifluoroacetic acid in the mobile phase). Fractions containing mixture of the two products were pooled, evaporated and dried in high vacuum. The residue was dissolved in water (5 ml) and lyophilized giving 526 mg of the product as a brown solid in form of TFA salt (49% yield relative to epoxide). Based on $^1$H NMR the product contained mixture of isomers (2R,3S,4S) (15a)/(2R,3S,4R) (15b) in ratio 1/1.

Elem. analysis: M.2.1TFA.0.5H$_2$O, calculated: C; (50.0), H; (5.5), N; (9.0), F; (15.5). found: C; (49.5), H; (5.3), N; (8.8), F; (16.0).

HRMS (ESI) m/z: [(M+H)$^+$] (C$_{28}$H$_{40}$O$_5$N$_5$) calculated: 526.30240. found: 526.30161.

Preparation of dibenzyl (2R,3S,4S)-4-hydroxy-3-(4,7,10-tris(2-(tert-butoxy)-2-oxoethyl)-1,4,7,10-tetraazacyclododecan-1-yl)pyrrolidine-1,2-dicarboxylate (15c) and dibenzyl (2R,3S,4R)-3-hydroxy-4-(4,7,10-tris(2-(tert-butoxy)-2-oxoethyl)-1,4,7,10-tetraazacyclododecan-1-yl)pyrrolidine-1,2-dicarboxylate (15d)

15d

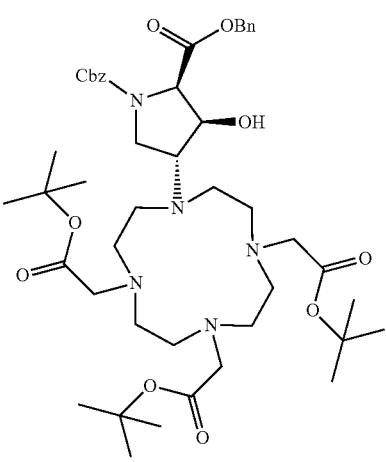

A mixture of isomers 15a and 15b in ratio 1/1 (426 mg, 0.563 mmol), t-butyl bromoacetate (341 uL, 2.31 mmol), anhydrous cesium carbonate (1.1 g, 3.34 mmol) and acetonitrile (21.3 mL) were placed into a 100 mL round bottom flask and the mixture was stirred for 1 hour at room temperature. The solids were filtered off and the filtrate was concentrated on rotary evaporator. Resulting oil was purified on reversed-phase flash chromatography (C18 column, acetonitrile/water gradient with 0.1% trifluoroacetic acid in the mobile phase). Fractions containing mixture of the two products were pooled, evaporated and dried in high vacuum giving 535 mg of white solid. The product contained mixture of isomers (2R,3S,4S) (15c)/(2R,3S,4R) (15d) in ratio 1/1 (based on LC-MS) in the form of salt with TFA (87% yield, assuming composition M.2TFA).

HRMS (ESI) m/z: [(M+H)$^+$] (C$_{46}$H$_{70}$O$_{11}$N$_5$) calculated: 868.50663. found: 868.50611.

Preparation of (2R,3S,4S)-4-hydroxy-3-(4,7,10-tris(2-(tert-butoxy)-2-oxoethyl)-1,4,7,10-tetraazacyclododecan-1-yl)pyrrolidine-2-carboxylic acid (15e) and (2R,3R,4R)-3-hydroxy-4-(4,7,10-tris(2-(tert-butoxy)-2-oxoethyl)-1,4,7,10-tetraazacyclododecan-1-yl)pyrrolidine-2-carboxylic acid (15f)

15c

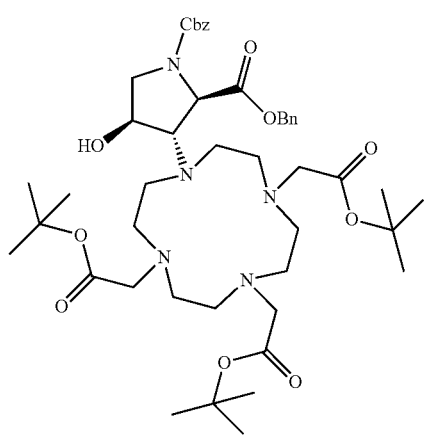

15e

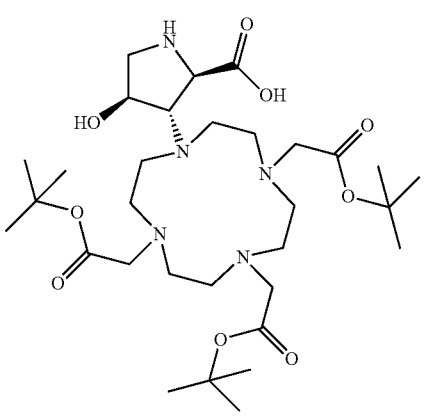

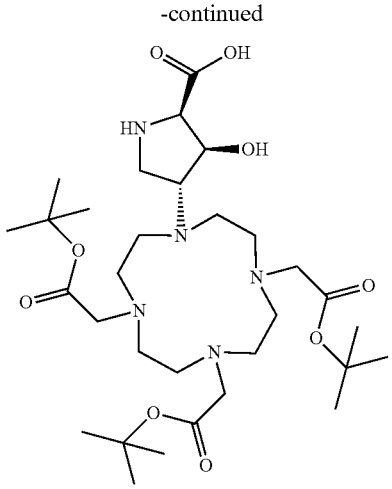

15f

The procedure was analogous to preparation of compounds 1g and 1h in Example 1. Reaction of the mixture of isomers 15c and 15d in ratio 1/1 (450 mg, 0.41 mmol), 10% Pd/C (37 mg, 0.346 mmol) in MeOH (34.6 mL) gave analogously 337 mg of the product as a white solid. The product contained mixture of isomers (2R,3S,4S) (15e)/(2R,3R,4R) (15f) in ratio 1/1 in the form of salt with TFA (95% yield, assuming composition M.2TFA).

HRMS (ESI) m/z: [(M+H)$^+$] (C$_{32}$H$_{58}$O$_9$N$_5$) calculated: 644.42290. found: 644.42197.

Example 16: Preparation of (2R,3S,4S)-1-(((9H-fluoren-9-yl)methoxy)carbonyl)-4-hydroxy-3-(4,7,10-tris(2-(tert-butoxy)-2-oxoethyl)-1,4,7,10-tetraazacyclododecan-1-yl)pyrrolidine-2-carboxylic acid (16)

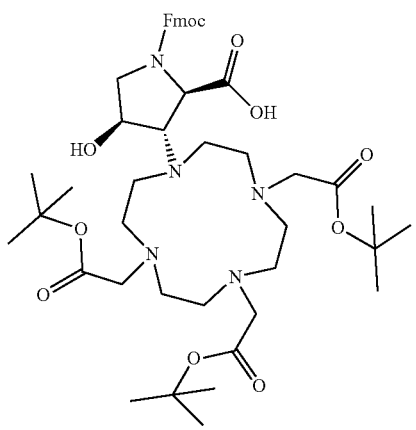

According to procedure in Example 2, reaction of a mixture of isomers 15e and 15f in ratio 1/1 (284 mg, 0.26 mmol), Fmoc chloride (78.0 mg, 0.30 mmol) in acetonitrile (16 mL) and borate buffer (15 mL, 0.2M, pH=9) was carried out. Chromatography analogously to Example 2 provided separation of the isomers (2R,3S,4S) and (2R,3S,4R). Fractions containing pure isomer (2S,3S,4S) were processed according to procedure in Example 2, giving analogously 57 mg of the product as a colorless solid in the form of salt with TFA (20% yield, assuming composition M.2TFA).

HRMS (ESI) m/z: [(M+H)$^+$] (C46H68O11N5) calculated: 866.49098. found: 866.49067.

$^1$H NMR (CD$_3$CN, 500 MHz, 318 K): $\delta_H$ 1.47-1.50 (tBu, m, 27H; 2.76-3.57 (proline arm, cycle, cycle carboxylate, m, 19H); 3.74-3.91 (proline arm, cycle carboxylate, m, 6H); 3.98-4.06 (proline arm, m, 1H) 4.13-4.17 (proline arm, m, 1H); 4.22-4.49 (fmoc, m, 3H); 7.32-7.37 (arom., m, 2H); 7.40-7.45 (arom., m, 2H); 7.62-7.68 (arom., m, 2H); 7.82-7.85 (arom., m, 2H). $^{13}$C{$^1$H} NMR (CD$_3$CN, 125 MHz, 318 K): 45.74-51.87 (cycle, m); 47.11 (fmoc, s); 50.64, 50.87 (proline arm, s); 54.41-54.85 (carboxylates, m); 56.67, 57.22 (proline arm, s); 67.27 (fmoc, s); 69.09-70.68 (proline arm, m); 82.75-84.41 (tBu, m) 119.97-120.03 (arom., m); 125.11-125.16 (arom., m); 127.19-127.24 (arom., m); 127.75-127.80 (arom., m); 141.08-141.26 (arom., m); 143.99, 144.06, 144.16, 144.26 (arom., s); 153.89, 154.57 (N—COO); 167.10, 170.33 (COOtBu); 172.43 (COOH, s)

Example 17: Preparation of (2R,3S,4R)-1-(((9H-fluoren-9-yl)methoxy)carbonyl)-3-hydroxy-4-(4,7,10-tris(2-(tert-butoxy)-2-oxoethyl)-1,4,7,10-tetraazacyclododecan-1-yl)pyrrolidine-2-carboxylic acid (17)

Compound was prepared as the second isomer (2S,3S,4R) by procedure in Example 16, obtaining 40 mg of product as a colorless solid in the form of salt with TFA (14% yield, assuming composition M.2TFA).

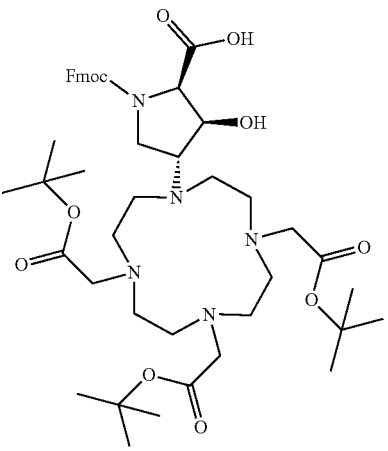

HRMS (ESI) m/z: [(M+H)$^+$] (C46H68O11N5) calculated: 866.49098. found: 866.49086.

Example 18: Preparation of 2,2',2''-(10-((2R,3S,4S)-1-(((9H-fluoren-9-yl)methoxy)carbonyl)-2-carboxy-4-hydroxypyrrolidin-3-yl)-1,4,7,10-tetraazacyclodo-decane-1,4,7-triyl)triacetic acid (18)

According to procedure in Example 3, reaction of starting compound 16 prepared in Example 16 (57 mg, 0.052 mmol) in TFA (2 mL, 26.14 mmol) gave analogously 35 mg of the product as a white fluffy solid in the form of salt with TFA (73% yield, assuming composition M.2TFA).

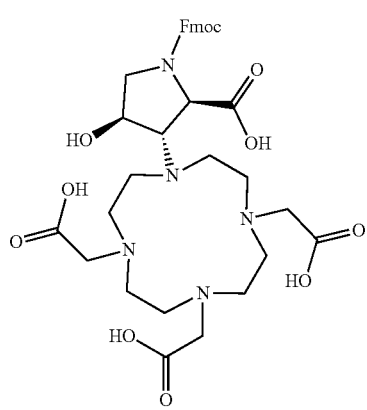

HRMS (ESI) m/z: [(M+H)$^+$] (C$_{34}$H$_{44}$O$_{11}$N$_5$) calculated: 698.30318. found: 698.30267.

Example 19: Preparation of 2,2',2"-(1-((3R,4S,5R)-1-(((9H-fluoren-9-yl)methoxy)carbonyl)-5-carboxy-4-hydroxypyrrolidin-3-yl)-1,4,7,10-tetraazacyclododecane-1,4,7-triyl)triacetic acid (19)

According to procedure in Example 3, reaction of starting compound 17 prepared in Example 17 (40 mg, 0.036 mmol) in TFA (2 mL, 26.14 mmol) gave analogously 22 mg of the product as a white fluffy solid in the form of salt with TFA (66% yield, assuming composition M.2TFA).

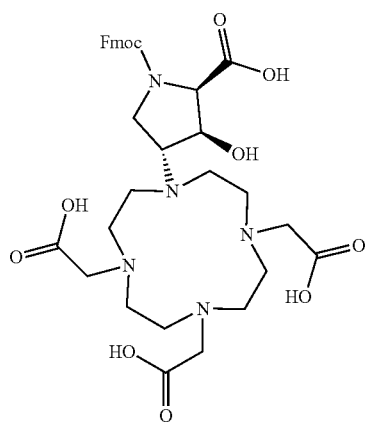

HRMS (ESI) m/z: [(M+H)$^+$] (C$_{34}$H$_{44}$O$_{11}$N$_5$) calculated: 698.30318. found: 698.30269.

$^1$H NMR (DMSO-d$_6$, 500 MHz): $\delta_H$ 2.85-3.52 (cycle+proline arm, m, 17H); 3.55-4.10 (proline arm+carboxylates, m, 8H); 4.11-4.40 (proline arm+fmoc, m, 4H); 4.60-4.74 (proline arm, m, 1H) 7.31-7.37 (arom., m, 2H); 7.41-7.44 (arom., m, 2H); 7.64-7.68 (arom., m, 2H); 7.88-7.91 (arom., m, 2H). $^{13}$C{$^1$H} NMR (DMSO-d$_6$, 125 MHz): 45.68-54.03 (cycle+carboxylates, m); 46.71, 46.79 (fmoc, s); 53.66, 53.91 (carboxylates, s); 62.32, 62.58 (proline arm, s); 67.36, 67.50 (fmoc, s); 68.97, 69.60 (proline arm, s); 120.36-120.47 (arom., m); 125.52-125.73 (arom., m); 127.40-127.59 (arom., m); 127.97-128.05 (arom., m); 140.86, 140.88, 140.92, 140.95 (arom., s); 143.73, 143.77, 143.88, 144.00 (arom., s); 153.84, 154.16 (N—COO); 170.52 (CH$_2$—COO); 171.36, 171.65 (COO).

Example 20: Preparation of Gd(III) complex of 2,2',2"-(10-((2R,3S,4S)-1-(((9H-fluoren-9-yl)methoxy)carbonyl)-2-carboxy-4-hydroxypyrrolidin-3-yl)-1,4,7,10-tetraazacyclododecane-1,4,7-triyl)triacetic acid (Gd-18)

According to procedure in Example 4, reaction of starting compound 18 prepared in Example 18 (5 mg, 0.005 mmol) in methanol (500 uL) and water (500 uL) with aqueous solution of GdCl$_3$ (50 uL, 0.1 M) and aqueous solution of N-methyl morpholine (353 uL, 0.1 M) gave analogously 3 mg of the product as a white solid (70% yield relative to 18).

HRMS (ESI) m/z: [(M+H)$^+$] (C$_{34}$H$_{41}$O$_{11}$N$_5$GdNa) calculated: 853.20381. found: 853.20420.

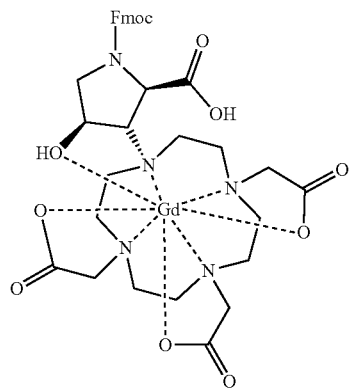

Example 21: Preparation of Gd(III) Complex of 2,2',2"-(10-((3R,4S,5R)-1-(((9H-fluoren-9-yl)methoxy)carbonyl)-5-carboxy-4-hydroxypyrrolidin-3-yl)-1,4,7,10-tetraazacyclododecane-1,4,7-triyl)triacetic acid (Gd-19)

According to procedure in Example 4, reaction of starting compound 19 prepared in Example 19 (5 mg, 0.005 mmol) in methanol (500 uL) and water (500 uL) with aqueous solution of GdCl$_3$ (50 uL, 0.1 M) and aqueous solution of N-methyl morpholine (353 uL, 0.1 M) gave analogously 2 mg of the product as a white solid (47% yield relative to 19).

HRMS (ESI) m/z: [(M+Na)$^+$] (C$_{34}$H$_{40}$O$_{11}$N$_5$GdNa) calculated: 875.18575, found: 875.18740.

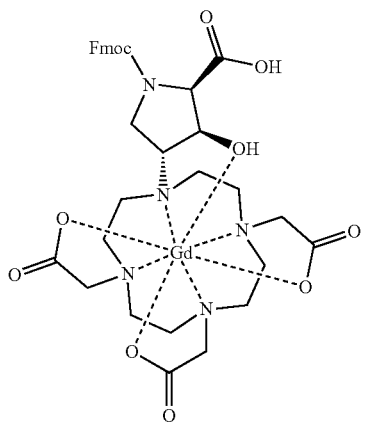

General Procedure for Peptide Couplings

Fmoc protected Rink Amide resin (TentaGel® R RAM, Rapp Polymere) resin (5 mg, 1 umol) was swelled for 30 minutes in 500 ul DMF. DMF was then removed. Then, 20% piperidine in DMF (500 ul) was used for deprotection for 2 minutes. After that the resin was washed with DMF (3×300 uL), DCM (3×300 uL) and DMF (3×300 uL).

For coupling of commercial amino acids, the procedure was as follows: Stock solutions were prepared in DMF of the amino acid (100 mg/mL) and of HATU (100 mg/mL). Coupling reaction was carried out by mixing the stock solution of amino acid, stock solution of HATU, neat DIPEA and DMF with the deprotected resin to reach the following final concentrations: 100 mM amino acid, 90 mM HATU and 300 mM DIPEA. The reaction mixture was let shaking for 30 minutes at room temperature after which the liquids were separated from the resin and the resin was washed with DMF (3×300 uL), DCM (3×300 uL) and DMF (3×300 uL).

For coupling of chelator or chelate building blocks, the procedure was as follows: Stock solutions were prepared in DMF of the chelator or chelate building block (100 mg/mL) and of HATU (100 mg/mL). Coupling reaction was carried out by mixing the stock solution of the building block, stock solution of HATU, neat DIPEA and NMP with the deprotected resin to reach the following final concentrations: 50 mM amino acid, 45 mM HATU and 150 mM DIPEA. The reaction mixture was let shaking for 60 minutes at room temperature after which the liquids were separated from the resin and the resin was washed with DMF (3×300 uL), DCM (3×300 uL), DMF (3×300 uL), MeOH (3×300 uL), DMF (3×300 uL), DCM (3×300 uL), DMF (3×300 uL).

General Procedure for Cleavage of Peptides from Resin Support

Peptides were cleaved from solid support by 500 uL of 47.5% TFA, 50% DCM, 2.5% triisopropyl silane mixture at room temperature for 1 hour. After that liquids were filtered off and the resin was washed with 40% solution of water in acetonitrile.

Example 22: Preparation of Dipeptide (Gd-3)-Gly-NH$_2$

According to the general procedure for peptide couplings, the synthesis was carried out in these steps:
1. Coupling: resin (5 mg, 1 umol), Fmoc-Gly-OH (2.3 mg, 7.6 umol), HATU (2.6 mg, 6.8 umol), DIPEA (4 ul, 22.8 umol).
2. Coupling: Compound Gd-3 (3.4 mg, 3.8 umol), HATU (1.3 mg, 3.4 umol), DIPEA (2 ul, 11.4 umol), NMP (54 uL).

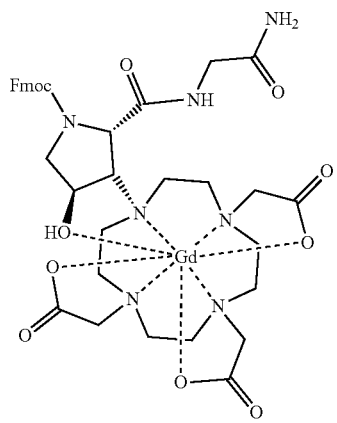

LCMS (ESI) m/z: [M+2H$^+$]$^{2+}$ (C$_{36}$H$_{45}$O$_{11}$N$_7$Gd) calculated: 455.1. found: 454.7.

Example 23: Preparation of Dipeptide (Gd-3)-Pro-NH$_2$

According to the general procedure for peptide couplings, the synthesis was carried out in these steps:
1. Coupling: resin (5 mg, 1 umol), Fmoc-Pro-OH (2.7 mg, 7.6 umol), HATU (2.6 mg, 6.8 umol), DIPEA (4 ul, 22.8 umol).
2. Coupling: Compound Gd-3 (3.4 mg, 3.8 umol), HATU (1.3 mg, 3.4 umol), DIPEA (2 ul, 11.4 umol), NMP (54 uL).

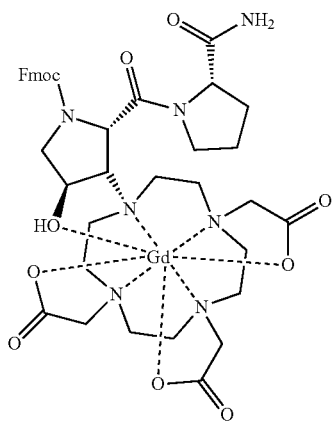

LCMS (ESI) m/z: [(M−H)$^-$] (C$_{39}$H$_{47}$O$_{11}$N$_7$Gd) calculated: 947.3. found: 947.3.

Example 24: Preparation of Dipeptide (Gd-3)-Phe-NH$_2$

According to the general procedure for peptide couplings, the synthesis was carried out in these steps:
1. Coupling: resin (5 mg, 1 umol), Fmoc-Phe-OH (2.9 mg, 7.6 umol), HATU (2.6 mg, 6.8 umol), DIPEA (4 ul, 22.8 umol).
2. Coupling: Compound Gd-3 (3.4 mg, 3.8 umol), HATU (1.3 mg, 3.4 umol), DIPEA (2 ul, 11.4 umol), NMP (54 uL).

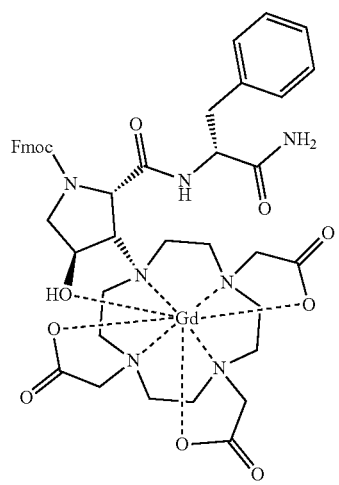

LCMS (ESI) m/z: [(M−H)⁻] (C₄₃H₄₉O₁₁N₇Gd) calculated: 997.3. found: 997.2.

Example 25: Preparation of Dipeptide (Gd-3)-Trp-NH₂

According to the general procedure for peptide couplings, the synthesis was carried out in these steps:
1. Coupling: resin (5 mg, 1 umol), Fmoc-Trp-OH (4.0 mg, 7.6 umol), HATU (2.6 mg, 6.8 umol), DIPEA (4.0 g, 22.8 umol).
2. Coupling: Compound Gd-3 (3.4 mg, 3.8 umol), HATU (1.3 mg, 3.4 umol), DIPEA (2 ul, 11.4 umol), NMP (54 uL).

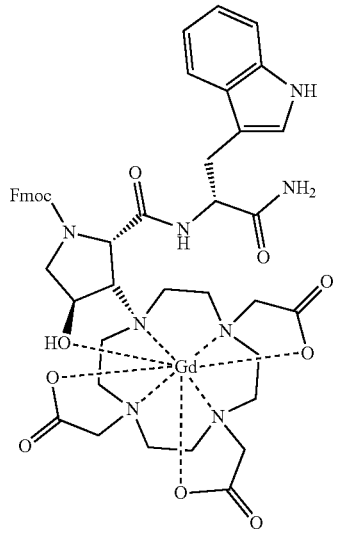

LCMS (ESI) m/z: [(M−H)⁻] (C₄₅H₅₀O₁₁N₈Gd) calculated: 1036.3. found: 1036.2.

Example 26: Preparation of Dipeptide (2)-Phe-OH

WANG resin preloaded with phenylalanine (3.8 mg, 0.8 umol) was treated with solution (1 mg/30 uL in DMF) of compound 14 (1 mg, 1 umol). After that solution (1 mg/20 uL in DMF) of HATU (0.4 mg, 1 umol) and 100 uL of 20% solution of N-methylmorpholine was added. The reaction mixture was let shaking for 1 h at room temperature after which the liquids were separated from the resin and the resin was washed with DMF (3×300 uL), NO DCM (3×300 uL) and DMF (3×300 uL). The product was cleaved from resin by mixture of 47.5% TFA, 50% DCM, 2.5% triisopropyl silane at room temperature for 1 hour. Although compound 14 was used in the synthesis, the removal of tert-butyldimethylsilyl protective group during cleavage from the resin makes it a derivative of compound 2 in the final product.

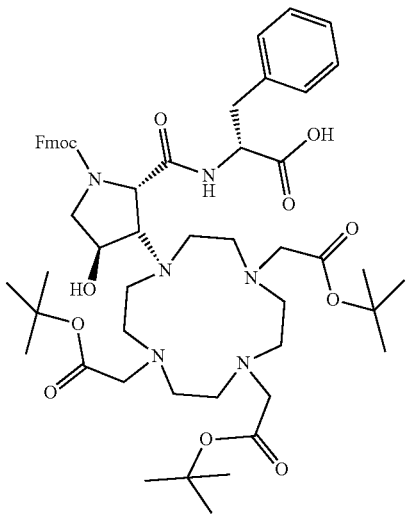

LCMS (ESI) m/z: [(M−H)⁻] (C₅₅H₇₅O₁₂N₆) calculated: 1011.6. found: 1011.5.

Example 27: Preparation of Dipeptide (8)-Phe-OH

WANG resin preloaded with phenylalanine (3.8 mg, 0.8 umol) was treated with solution (1 mg/30 uL in DMF) of compound 8 (1 mg, 1 umol). After that solution (mg/20 uL in DMF) of HATU (0.4 mg, 1 umol) and 100 uL of 20% solution of N-methylmorpholine was added. The reaction mixture was let shaking for 1 h at room temperature after which the liquids were separated from the resin and the resin was washed with DMF (3×300 uL), DCM (3×300 uL) and DMF (3×300 uL). The product was cleaved from resin by mixture of 47.5% TFA, 50% DCM, 2.5% triisopropyl silane at room temperature for 1 hour.

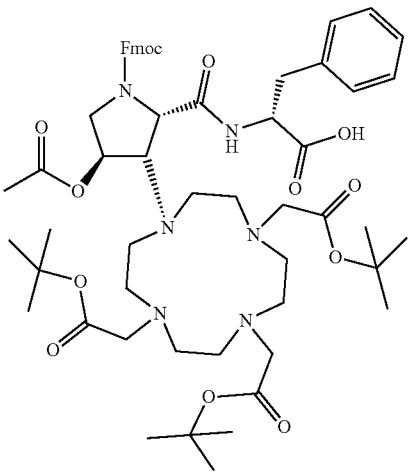

LCMS (ESI) m/z: [(M−H)⁻] (C₅₇H₇₇O₁₃N₆) calculated: 1053.6. found: 1053.5.

Example 28: Preparation of Pentapeptide (12)-Gly-Phe-(Gd-6)-Gly-NH₂

According to the general procedure for peptide couplings, the synthesis was carried out in these steps:

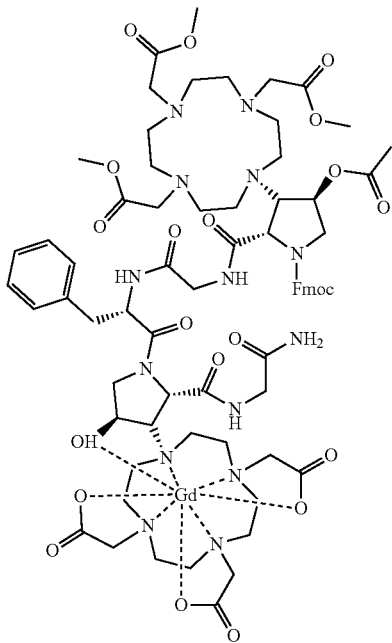

1. Coupling: resin (10 mg, 2 umol), Fmoc-Gly-OH (4.5 mg, 15.2 umol), HATU (5.2 mg, 13.7 umol), DIPEA (8 ul, 45.6 umol).
2. Coupling: Gd-3 (6.75 mg, 7.6 umol), HATU (2.6 mg, 6.8 umol), DIPEA (4 ul, 22.8 umol), NMP (54 uL).
3. Coupling: Gd-3 (6.75 mg, 7.6 umol), HATU (2.6 mg, 6.8 umol), DIPEA (4 ul, 22.8 umol), NMP (54 uL).
4. Coupling: Fmoc-Phe-OH (5.9 mg, 15.2 umol), HATU (5.2 mg, 13.7 umol), DIPEA (8 ul, 45.6 umol).
5. Coupling: Fmoc-Gly-OH (4.5 mg, 15.2 umol), HATU (5.2 mg, 13.7 umol), DIPEA (8 ul, 45.6 umol).
6. Resin was treated with 0.1 M solution of LiOH in MeOH (500 uL) for 2 hours at room temperature, followed by wash with MeOH (3×300 uL) and wash sequence in general procedure.
7. Coupling: Compound 12 (7.7 mg, 7.6 umol), HATU (2.6 mg, 6.8 umol), DIPEA (4 ul, 22.8 umol), NMP (54 uL).
8. The product was cleaved from resin by mixture of 47.5% TFA, 50% DCM, 2.5% triisopropyl silane at room temperature for 1 hour.

Product was purified by preparative HPLC (C18 column, acetonitrile/water gradient with 0.1% formic acid in the mobile phase). Fractions containing pure product were pooled, evaporated, the residue was dissolved in water (1 mL) and lyophilized to give 0.3 mg of product as white fluffy solid. Although compound Gd-3 was used in the synthesis, the removal of Fmoc protective group makes it a derivative of compound Gd-6 in the final product.

HRMS (ESI) m/z: [z=2 $(M+H+Na)^{2+}$] ($C_{71}H_{96}O_{22}N_{14}GdNa$) calculated: 838.79757. found: 838.79781.

Example 29: Preparation of Pentapeptide (6)-Gly-Phe-(Gd-6)-Gly-NH$_2$

Pentapeptide (12)-Gly-Phe-(Gd-6)-Gly-NH$_2$ prepared in Example 28 was dissolved in water (1 mL) and aqueous solution of LiOH (500 uL, 1M) was added. Reaction mixture was stirred for 30 minutes at room temperature. Then, neat formic acid (19 uL) was added. Product was purified by preparative HPLC (C18 column, acetonitrile/water gradient with 0.1% formic acid in the mobile phase). Fractions containing pure product were pooled and evaporated. The reaction removed methyl ester groups and Fmoc simultaneously, thus converting the N-terminal chelator amino acid in the product to a derivative of compound 6.

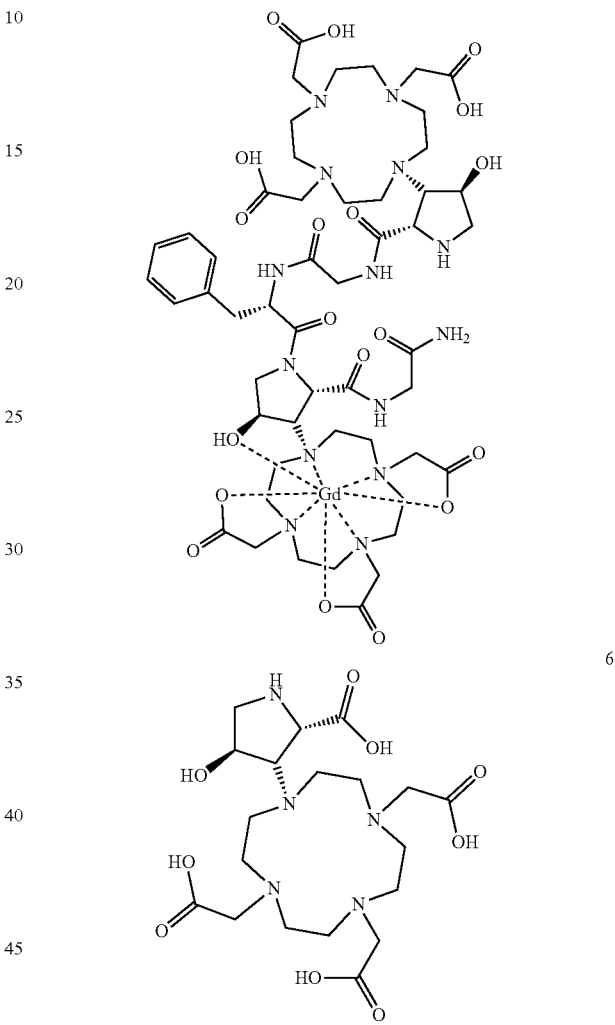

HRMS (ESI) m/z: [z=2 $(M+2H)^{2+}$] ($C_{51}H_{79}O_{19}N_{14}Gd$) calculated: 674.74380. found: 674.74361.

Example 30: Preparation of Pentapeptide (Lu-6)-Gly-Phe-(Gd-6)-Gly-NH$_2$

Pentapeptide (6)-Gly-Phe-(Gd-6)-Gly-NH$_2$ prepared in Example 29 was dissolved in water (2 mL), aqueous solution of LuCl$_3$ (8 uL, 0.04683 M) and aqueous solution of N-methyl morpholine (216 uL, 0.1 M) were added and the reaction mixture was stirred at room temperature for 1 hour. Product was purified by preparative HPLC (C18 column, acetonitrile/water gradient with 0.1% formic acid in the mobile phase). Fractions containing pure product were pooled, evaporated, the residue was dissolved in water (1 mL) and lyophilized to give 0.1 mg of product as white fluffy solid. Complexation of Lu(III) converted the N-terminal chelator amino acid in the product to a derivative of Lu-6, which is analogous to Gd-6 from Example 6, with the exception that Gd is replaced with Lu.

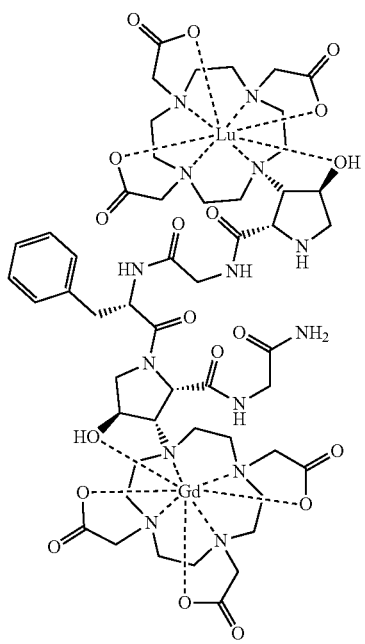

HRMS (ESI) m/z: [(M+H)$^+$] (C$_{51}$H$_{75}$O$_{19}$N$_{14}$GdLu) calculated: 1520.39761. found: 1520.39719.

Example 31: Preparation of tetrapeptide Gly-Phe-(Gd-6)-Gly-NH$_2$

According to the general procedure for peptide couplings, the synthesis was carried out in these steps:

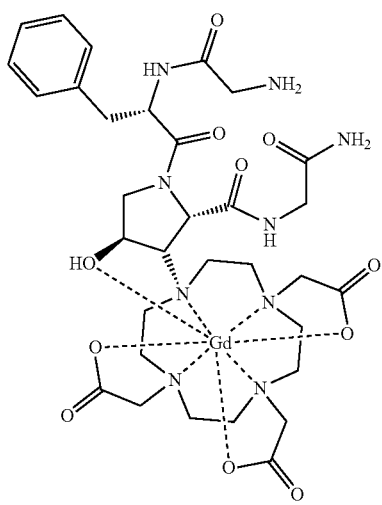

1. Coupling: resin (20 mg, 4 umol), Fmoc-Gly-OH (9 mg, 30.4 umol), HATU (10.4 mg, 27.4 umol), DIPEA (16 ul, 91.2 umol).
2. Coupling: Gd-3 (13.5 mg, 15.2 umol), HATU (5.2 mg, 13.7 umol), DIPEA (8 ul, 45.6 umol), NMP (109 uL).
3. Coupling: Gd-3 (13.5 mg, 15.2 umol), HATU (5.2 mg, 13.7 umol), DIPEA (8 ul, 45.6 umol), NMP (109 uL).
4. Coupling: Fmoc-Phe-OH (11.8 mg, 30.4 umol), HATU (10.4 mg, 27.4 umol), DIPEA (16 ul, 91.2 umol).
5. Coupling: Fmoc-Gly-OH (9 mg, 30.4 umol), HATU (10.4 mg, 27.4 umol), DIPEA (16 ul, 91.2 umol).
6. The product was cleaved from resin by mixture of 47.5% TFA, 50% DCM, 2.5% triisopropyl silane at room temperature for 1 hour.

Product was purified by preparative HPLC (C18 column, acetonitrile/water gradient with 0.1% formic acid in the mobile phase). Fractions containing pure product were pooled, evaporated, the residue was dissolved in water (1 mL) and lyophilized to give 0.1 mg of product as white fluffy solid. Although compound Gd-3 was used in the synthesis, the removal of Fmoc protective group makes it a derivative of compound Gd-6 in the final product.

HRMS (ESI) m/z: [(M+H)$^+$] (C$_{33}$H$_{47}$O$_{11}$N$_9$Gd) calculated: 891.26306. found: 891.26321.

Example 32: Preparation of Tetrapeptide Gly-Phe-(Lu-6)-Gly-NH$_2$

According to the general procedure for peptide couplings, the synthesis was carried out in these steps:

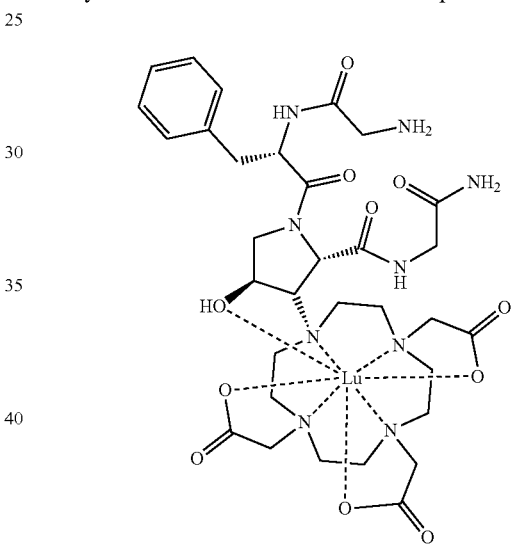

1. Coupling: resin (10 mg, 2 umol), Fmoc-Gly-OH (4.5 mg, 15.2 umol), HATU (5.2 mg, 13.7 umol), DIPEA (8 ul, 45.6 umol).
2. Coupling: Lu-3 (6.79 mg, 7.6 umol), HATU (2.6 mg, 6.8 umol), DIPEA (4 ul, 22.8 umol), NMP (54 uL).
3. Coupling: Fmoc-Phe-OH (5.9 mg, 15.2 umol), HATU (5.2 mg, 13.7 umol), DIPEA (8 ul, 45.6 umol).
4. Coupling: Fmoc-Gly-OH (4.5 mg, 15.2 umol), HATU (5.2 mg, 13.7 umol), DIPEA (8 ul, 45.6 umol).
5. The product was cleaved from resin by mixture of 47.5% TFA, 50% DCM, 2.5% triisopropyl silane at room temperature for 1 hour.

Product was purified by preparative HPLC (C18 column, acetonitrile/water gradient with 0.1% formic acid in the mobile phase). Fractions containing pure product were pooled, evaporated, the residue was dissolved in water (1 mL) and lyophilized. Although compound Lu-3 was used in the synthesis, the removal of Fmoc protective group makes it a derivative of compound Lu-6 in the final product, which is analogous to Gd-6 from Example 6, with the exception that Gd is replaced with Lu.

LC-MS (ESI) m/z: [(M+H)⁺] ($C_{32}H_{47}O_{11}N_9$) calculated: 908.3. found: 908.3.

II. Properties of Gd(II) Chelates

Example 33: Relaxivity of Gd(III) Chelates

Relaxivity of Gd(III) chelate Gd-6 and of a peptide Gly-Phe-(Gd-6)-Gly-NH₂ have been measured at 40° C. and 0.5 T in 10 mM MOPS buffer pH=7.0. Table 1 summarizes the results. It is apparent from the data that the relaxivity of the peptide, where the Gd-6 is incorporated within the peptide chain, is higher than the relaxivity of a standalone Gd-6. This demonstrates that covalent linkage of the chelate Gd-6 to molecular chains through peptide bonds provides the means to increase relaxivity. For comparison, relaxivity of most clinically used MRI contrast agents at comparable conditions is within the range 3-4 $mM^{-1}\ s^{-1}$ (Rohrer M. (2005), *Invest. Radiol.* 40, 715-724). The relaxivity of peptide Gly-Phe-(Gd-6)-Gly-NH₂ is above this range despite of its relatively small size.

TABLE 1

| Gd compound | Gd concentration c (mM) * | Relaxation time $T_1$ (ms) | Relaxivity $r_1$ ($mM^{-1} \cdot s^{-1}$) at 40° C., and 0.5 T ** |
|---|---|---|---|
| Gd-6 (Example 6) | 0.087 | 1562 | 3.5 |
| Peptide Gly-Phe-(Gd-6)-Gly-NH₂ (Example 31) | 0.138 | 1004 | 4.8 |

* Determined by ICP-AES.
** Calculated $r_1 = R_1/c$, where c is Gd concentration in mM, and $R_1 = 1/(T_1/1000) - 1/(T_{1D}/1000)$, where $T_1$ is the relaxation time of the sample (in ms) and $T_{1D}$ is the relaxation time of the buffer without Gd.

Example 34: Kinetic Inertness of the Building Block Gd-3

Stability (kinetic inertness) of the Gd(III) building block Gd-3 prepared in Example 4 was tested by following acid-assisted decomplexation by HPLC. Isocratic elution method was used for analysis. Constant concentration of TFA (0.08%) was maintained in the mobile phase (pH ~2.0), while methanol content was varied to tune the retention time of the analyte. With increasing retention time (i.e. time spent in the acidic medium), more decomplexation should occur and the amount of intact chelate should decrease mono-exponentially (pseudo first-order reaction conditions), while a peak of free chelator should appear in the chromatogram. The HPLC conditions were as follows: column Kinetex C18, 100×3 mm, 2.6 um; column temperature maintained at 40° C.; mobile phase: TFA (constant 0.08% vol.), MeOH (variable), water; flow-rate 0.6 mL/min; UV detection at 280 nm; injection of 2 uL of 0.5 mM sample. Table 2 summarizes the results, showing that there was no decrease in the peak area of the intact chelate Gd-3, thus demonstrating high kinetic inertness of Gd-3 under acidic conditions.

TABLE 2

| Methanol in mobile phase (%) | Retention time (min) | Peak area (mAU · s) |
|---|---|---|
| 40 | 4.632 | 681.6 |
| 39 | 5.044 | 685.5 |
| 38 | 5.570 | 688.4 |
| 37 | 6.072 | 686.6 |
| 36 | 6.894 | 690.9 |

---

The invention claimed is:

1. A cyclen based compound of general formula (I),

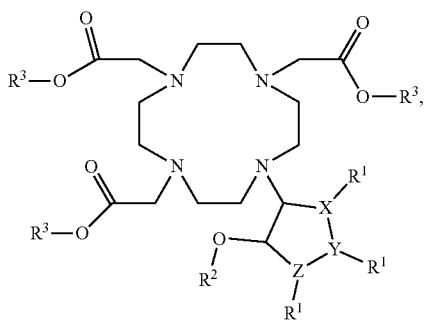

wherein

X is nitrogen and Y, Z are —CH—, or X, Z are —CH— and Y is nitrogen, or X, Y are —CH— and Z is nitrogen;

$R^1$ is independently selected from H; COOH; benzyloxycarbonyl; fluorenylmethyloxycarbonyl; tertbutoxycarbonyl; methylcarbonyl; trifluoromethylcarbonyl; benzyl; triphenylmethyl; tosyl; mesyl;

benzyloxymethyl; phenylsulfonyl; ethoxycarbonyl; 2,2,2-trichloroethyloxycarbonyl; methoxycarbonyl; methoxymethyloxycarbonyl;

$R^2$ is selected from H; methylcarbonyl; tert-butyldimethylsilyl; (C1-C4)alkyl, which can be linear or branched, and which can optionally be substituted with $CH_3O$—, $CH_3S$—; oxacyclohexyl; allyl; tert-butyldiphenylsilyl; tertbutylcarbonyl; phenylcarbonyl; nitrobenzyl; benzyloxymethyl, which can optionally be substituted with $CH_3O$—, —$NO_2$; fluorenylmethyloxycarbonyl; trichlorocarbonyl; trifluorocarbonyl; benzyl; tosyl; mesyl; phenylsulfonyl; allylsulphonyl; ethoxycarbonyl; 2,2,2-trichloroethyloxycarbonyl; methoxycarbonyl; methoxymethyloxycarbonyl;

$R^3$ is independently selected from H; (C1-C6)alkyl, which can be linear or branched, and which can optionally be substituted with —$CH_3$, —Cl, —F, —CN, tosyl, triisopropylsilyl, $CH_3O$—, $CH_3S$—; (C5-C6)cycloalkyl, which can optionally be substituted with —$CH_3$, —Cl, —F, —CN; (C6-C10)aryl, which can optionally be substituted with —$CH_3$, —Cl, —F, —CN; allyl, propargyl; fluorenylmethyl; benzoylmethyl; phenyloxymethyl; oxacyclopentyl; 2-oxo-1,2-diphenylethyl;

with the proviso that where $R^1$ is bound to nitrogen, then $R^1$ is not COOH;

with the proviso that where $R^1$ is bound to —CH—, then $R^1$ is independently H or COOH;

with the proviso that one $R^1$ is COOH;

and with the proviso that one —CH—$R^1$ group is —$CH_2$—.

2. The cyclen based compound of general formula (I) according to claim 1, wherein Y is nitrogen, X—$R^1$ is —$CH_2$—, and Z—$R^1$ is —CH(COOH)—.

3. The cyclen based compound of general formula (I) according to claim 1, wherein Y is nitrogen, X—$R^1$ is —CH(COOH)—, and Z—$R^1$ is —$CH_2$—.

4. The cyclen based compound of general formula (I) according to claim 1, wherein X is nitrogen, Y—$R^1$ is —CH(COOH)—, and Z—$R^1$ is —$CH_2$—.

5. The cyclen based compound of general formula (I) according to claim 1, wherein X—$R^1$ is —$CH_2$—, Y—$R^1$ is —CH(COOH)—, and Z is nitrogen.

6. The cyclen based compound of general formula (I) according to claim 1, wherein $R^1$ is selected from H, COOH, benzyloxy carbonyl and fluorenylmethyloxycarbonyl.

7. The cyclen based compound of general formula (I) according to claim 1, wherein $R^2$ is selected from H, methylcarbonyl and tert-butyldimethylsilyl.

8. The cyclen based compound of general formula (I) according to claim 1, wherein $R^3$ is selected from H, methyl and tert-butyl.

9. The cyclen based compound of general formula (1) according to claim 1, wherein the compound of general formula (I) is selected from the group consisting of:

(2S,3S,4S)-4-hydroxy-3-(4,7,10-tris(2-(tert-butoxy)-2-oxoethyl)-1,4,7,10-tetraazacyclododecan-1-yl)pyrrolidine-2-carboxylic acid;

(2S,3R,4R)-3-hydroxy-4-(4,7,10-tris(2-(tert-butoxy)-2-oxoethyl)-1,4,7,10-tetraazacyclododecan-1-yl)pyrrolidine-2-carboxylic acid;

(2S,3S,4S)-1-(((9H-fluoren-9-yl)methoxy)carbonyl)-4-hydroxy-3-(4,7,10-tris(2-(tert-butoxy)-2-oxoethyl)-1,4,7,10-tetraazacyclododecan-1-yl)pyrrolidine-2-carboxylic acid;

2,2',2"-(10-((2S,3S,4S)-1-(2-(9H-fluoren-9-yl)acetoxy)-2-carboxy-4-hydroxypyrrolidin-3-yl)-1,4,7,10-tetraazacyclododecane-1,4,7-triyl)triacetic acid;

(2S,3S,4S)-4-acetoxy-3-(4,7,10-tris(2-(tert-butoxy)-2-oxoethyl)-1,4,7,10-tetraazacyclododecan-1-yl)pyrrolidine-2-carboxylic acid;

(2S,3R,4R)-3-acetoxy-4-(4,7,10-tris(2-(tert-butoxy)-2-oxoethyl)-1,4,7,10-tetraazacyclododecan-1-yl)pyrrolidine-2-carboxylic acid;

(2S,3S,4S)-1-(((9H-fluoren-9-yl)methoxy)carbonyl)-4-acetoxy-3-(4,740-tris(2-(tert-butoxy)-2-oxoethyl)-1,4,7,10-tetraazacyclododecan-1-yl)pyrrolidine-2-carboxylic acid:

2,2',2"-(10-((2S,3S,4S)-1-(((9H-fluoren-9-yl)methoxy)carbonyl)-4-acetoxy-2-carboxypyrrolidin-3-yl)-1,4,7,10-tetraazacyclododecane-1,4,7-triyl)triacetic acid;

(2S,3S,4S)-4-acetoxy-3-(4,7,10-tris(2-methoxy-2-oxoethyl)-1,4,7,10-tetraazacyclododecan-1-yl)pyrrolidine-2-carboxylic acid;

(2S,3R,4R)-3-acetoxy-4-(4,7,10-tris(2-methoxy-2-oxoethyl)-1,4,7,10-tetraazacyclododecan-1-yl)pyrrolidine-2-carboxylic acid;

(2S,3S,4S)-1-(((9H-fluoren-9-yl)methoxy)carbonyl)-4-acetoxy-3-(4,7,10-tris(2-tnethoxy-2-oxoethyl)-1,4,7,10-tetraazacyclododecan-1-yl)pyrrolidine-2-carboxylic acid;

(2S,3S,4S)-4-((tert-butyldimethylsilyl)oxy)-3-(4,7,10-tris(2-(tert-butoxy)-2-oxoethyl)-1,4,7,10-tetraazacyclododecan-1-yl)pyrrolidine-2-carboxylic acid;

(2S,3R,4R)-3-((tert-butyldimethylsilyl)oxy)-4-(4,7,10-tris(2-(tert-butoxy)-2-oxoethyl)-1,4,7,10-tetraazacyclododecan-1-yl)pyrrolidine-2-carboxylic acid;

(2S,3S,4S)-1-(((9H-fluoren-9-yl)methoxy)carbonyl)-4-((tert-butyldimethylsilyl)oxy)-3-(4,7,10-tris(2-(tert-butoxy)-2-oxoethyl)-1,4,7,10-tetraazacyclododecan-1-yl)pyrrolidine-2-carboxylic acid;

(2R,3S,4S)-4-hydroxy-3-(4,7,10-tis(2-(tert-butoxy)-2-oxoethyl)-1,4,7,10-tetraazacyclododecan-1-yl)pyrrolidine-2-carboxylic acid;

(2R,3R,4R)-3-hydroxy-4-(4,7,10-tris(2-(tert-butoxy)-2-oxoethyl)-1,4,7,10-tetraazacyclododecan-1-yl)pyrrolidine-2-carboxylic acid;

(2R,3S,4S)-1-(((9H-fluoren-9-yl)methoxy)carbonyl)-4-hydroxy-3-(4,7,10-tris(2-(tert-butoxy)-2-oxoethyl)-1,4,7,10-tetraazacyclododecan-1-yl)pyrrolidine-2-carboxylic acid;

(2R,3S,4R)-1-(((9H-fluoren-9-yl)methoxy)carbonyl)-3-hydroxy-4-(4,7,10-tris(2-(tert-butoxy)-2-oxoethyl)-1,4,7,10-tetraazacyclododecan-1-yl)pyrrolidine-2-carboxylic acid;

2,2',2"-(10-((2R,3S,4S)-1-(((9H-fluoren-9-yl)methoxy)carbonyl)-2-carboxy-4-hydroxypyrrolidin-3-yl)-1,4,7,10-tetraazacyclododecane-1,4,7-triyl)triacetic acid;

2,2',2"-(10-((3R,4S,5R)-1-(((9H-fluoren-9-yl)methoxy)carbonyl)-5-carboxy-4-hydroxypyrrolidin-3-yl)-1,4,7,10-tetraazacyclododecane-1,4,7-triyl)triacetic acid.

10. A coordination compound of general formula (1a),

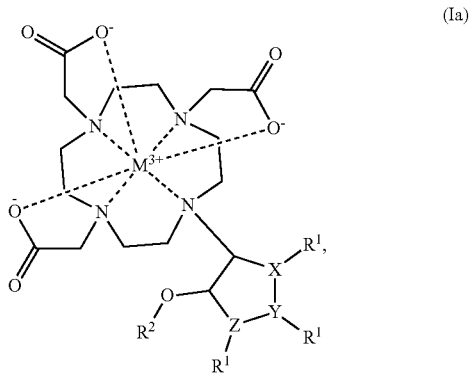

(Ia)

wherein
X is nitrogen and Y, Z are —CH—, or X, Z are —CH— and Y is nitrogen, or X, Y are —CH— and Z is nitrogen;

$R^1$ is independently selected from H; COOH; benzyloxycarbonyl; fluorenylmethyloxycarbonyl; tert-butoxycarbonyl; methylcarbonyl; trifluoromethylcarbonyl; benzyl; triphenylmethyl; tosyl; mesyl; benzyloxymethyl; phenylsulfonyl; ethoxycarbonyl; 2,2,2-trichloroethyloxycarbonyl; methoxycarbonyl; methoxymethyloxycarbonyl;

$R^2$ is selected from H; methylcarbonyl; tert-butyldimethylsilyl; (C1-C4)alkyl, which can be linear or branched, and which can optionally be substituted with $CH_3O$—, $CH_3S$—; oxacyclohexyl; allyl; tert-butyldiphenylsilyl; tert-butylcarbonyl; phenylcarbonyl; nitrobenzyl; benzyloxymethyl, which can optionally be substituted with $CH_3O$—, —$NO_2$; fluorenylmethyloxycarbonyl; trichlorocarbonyl; trifluorocarbonyl; benzyl; tosyl; mesyl; phenylsulfonyl; allylsulphonyl; ethoxycarbonyl; 2,2,2-trichloroethyloxycarbonyl; methoxycarbonyl; methoxymethyloxycarbonyl;

$M^{3+}$ is a metal cation selected from die group consisting of $In^{3+}$, $Ga^{3+}$, trivalent cations of rare earth elements, selected from lanthanide(III) cations, Y(IIT) and Sc(III), preferably the metal cation is selected from $Gd^{3+}$ and $Lu^{3+}$;

with the proviso that where $R^1$ is bound to nitrogen, then $R^1$ is not COOH;
with the proviso that where $R^1$ is bound to —CH—, then $R^1$ is independently H or COOH;
with the proviso that one $R^1$ is COOH; and
with the proviso that one —CH—$R^1$ group is —$CH_2$—.

11. A pharmaceutical preparation, characterized in that it contains at least one coordination compound according to claim 10, and a pharmaceutically acceptable auxiliary substance.

* * * * *

SEQUENCE LISTING

```
<160> NUMBER OF SEQ ID NOS: 5

<210> SEQ ID NO 1
<211> LENGTH: 5
<212> TYPE: PRT
<213> ORGANISM: artificial
<220> FEATURE:
<223> OTHER INFORMATION: Pentapeptide synthesised in Example 28.
<220> FEATURE:
<221> NAME/KEY: (12)
<222> LOCATION: (1)..(1)
<223> OTHER INFORMATION: (2S,3S,4S)-1-(((9H-fluoren-9-yl)methoxy)
      carbonyl)-4-acetoxy-3-(4,7,10-tris(2-methoxy-2-oxoethyl)-1,4,7,
      10-tetraazacyclododecan-1-yl)pyrrolidine-2-carboxylic acid
<220> FEATURE:
<221> NAME/KEY: (Gd-6)
<222> LOCATION: (4)..(4)
<223> OTHER INFORMATION: Gd(III) complex of
      2,2',2"-(10-((2S,3S,4S)-2-carboxy-4-hydroxypyrrolidin-3-yl)-1,4,
      7,10-tetraazacyclododecane-1,4,7-triyl)triacetic acid

<400> SEQUENCE: 1

Xaa Gly Phe Xaa Gly
1               5

<210> SEQ ID NO 2
<211> LENGTH: 5
<212> TYPE: PRT
<213> ORGANISM: artificial
<220> FEATURE:
<223> OTHER INFORMATION: Pentapeptide synthesised in Example 29.
<220> FEATURE:
```

<221> NAME/KEY: (6)
<222> LOCATION: (1)..(1)
<223> OTHER INFORMATION: 2,2',2"-(10-((2S,3S,4S)-(2-carboxy-4-
      hydroxypyrrolidin-3-yl)-1,4,7,10-tetraazacyclododecane-1,4,7-
      triyl)triacetic acid
<220> FEATURE:
<221> NAME/KEY: (Gd-6)
<222> LOCATION: (4)..(4)
<223> OTHER INFORMATION: Gd(III) complex of
      2,2',2"-(10-((2S,3S,4S)-2-carboxy-4-hydroxypyrrolidin-3-yl)-1,4,
      7,10-tetraazacyclododecane-1,4,7-triyl)triacetic acid

<400> SEQUENCE: 2

Xaa Gly Phe Xaa Gly
1               5

<210> SEQ ID NO 3
<211> LENGTH: 5
<212> TYPE: PRT
<213> ORGANISM: artificial
<220> FEATURE:
<223> OTHER INFORMATION: Pentapeptide synthesised in Example 30.
<220> FEATURE:
<221> NAME/KEY: (Lu-6)
<222> LOCATION: (1)..(1)
<223> OTHER INFORMATION: Lu(III) complex of
      2,2',2"-(10-((2S,3S,4S)-2-carboxy-4-hydroxypyrrolidin-3-yl)-1,4,
      7,10-tetraazacyclododecane-1,4,7-triyl)triacetic acid
<220> FEATURE:
<221> NAME/KEY: (Gd-6)
<222> LOCATION: (4)..(4)
<223> OTHER INFORMATION: Gd(III) complex of
      2,2',2"-(10-((2S,3S,4S)-2-carboxy-4-hydroxypyrrolidin-3-yl)-1,4,
      7,10-tetraazacyclododecane-1,4,7-triyl)triacetic acid

<400> SEQUENCE: 3

Xaa Gly Phe Xaa Gly
1               5

<210> SEQ ID NO 4
<211> LENGTH: 4
<212> TYPE: PRT
<213> ORGANISM: artificial
<220> FEATURE:
<223> OTHER INFORMATION: Tetrapeptide synthesised in Example 31.
<220> FEATURE:
<221> NAME/KEY: (Gd-6)
<222> LOCATION: (3)..(3)
<223> OTHER INFORMATION: Gd(III) complex of
      2,2',2"-(10-((2S,3S,4S)-2-carboxy-4-hydroxypyrrolidin-3-yl)-1,4,
      7,10-tetraazacyclododecane-1,4,7-triyl)triacetic acid

<400> SEQUENCE: 4

Gly Phe Xaa Gly
1

<210> SEQ ID NO 5
<211> LENGTH: 4
<212> TYPE: PRT
<213> ORGANISM: artificial
<220> FEATURE:
<223> OTHER INFORMATION: Tetrapeptide synthesised in Example 32.
<220> FEATURE:
<221> NAME/KEY: (Lu-6)

```
<222> LOCATION: (3)..(3)
<223> OTHER INFORMATION: Lu(III) complex of
    2,2',2"-(10-((2S,3S,4S)-2-carboxy-4-hydroxypyrrolidin-3-yl)-1,4,
    7,10-tetraazacyclododecane-1,4,7-triyl)triacetic acid

<400> SEQUENCE: 5

Gly Phe Xaa Gly
1
```